United States Patent
Johnson

(10) Patent No.: US 8,556,969 B2
(45) Date of Patent: Oct. 15, 2013

(54) BIOCOMPATIBLE COPPER-BASED SINGLE-CRYSTAL SHAPE MEMORY ALLOYS

(75) Inventor: Alfred David Johnson, San Leandro, CA (US)

(73) Assignee: Ormco Corporation, Orange, CA (US)

( * ) Notice: Subject to any disclaimer, the term of this patent is extended or adjusted under 35 U.S.C. 154(b) by 68 days.

(21) Appl. No.: 12/325,722

(22) Filed: Dec. 1, 2008

(65) Prior Publication Data

US 2009/0187243 A1 Jul. 23, 2009

Related U.S. Application Data

(60) Provisional application No. 60/991,634, filed on Nov. 30, 2007.

(51) Int. Cl.
*A61F 2/00* (2006.01)

(52) U.S. Cl.
USPC ........ 623/11.11; 148/562; 148/563; 148/402; 427/2.27; 427/453; 427/529

(58) Field of Classification Search
USPC ...................... 623/11.11; 148/562, 563, 402; 427/2.27, 453, 529
See application file for complete search history.

(56) References Cited

U.S. PATENT DOCUMENTS

| | | | |
|---|---|---|---|
| 368,425 A | 8/1887 | Ross et al. | |
| 538,593 A | 4/1895 | Naylor, Jr. | |
| 1,560,335 A | 11/1925 | Czochralski | |
| 1,904,828 A | 4/1933 | Green | |
| 1,913,035 A | 6/1933 | Loepsinger | |
| 1,926,925 A | 9/1933 | Wescott | |
| 2,060,593 A | 11/1936 | Schaurte et al. | |
| 2,371,614 A | 3/1945 | Graves | |
| 2,586,556 A | 2/1952 | Mullikin | |
| 2,608,996 A | 9/1952 | Forman | |
| 2,610,300 A | 9/1952 | Walton et al. | |

(Continued)

FOREIGN PATENT DOCUMENTS

| | | |
|---|---|---|
| EP | 0053596 | 6/1982 |
| EP | 0310439 | 4/1989 |

(Continued)

OTHER PUBLICATIONS

Antonov et al.; New advances and developments in the Stepnakov method for the growth of shaped crystals; Crystallography Reports; vol. 47; Suppl. 1; 2002; pp. S43-S52.

(Continued)

*Primary Examiner* — David Isabella
*Assistant Examiner* — Suba Ganesan
(74) *Attorney, Agent, or Firm* — Wood, Herron & Evans, LLP

(57) ABSTRACT

We describe herein biocompatible single crystal Cu-based shape memory alloys (SMAs). In particular, we show biocompatibility based on MEM elution cell cytotoxicity, ISO intramuscular implant, and hemo-compatibility tests producing negative cytotoxic results. This biocompatibility may be attributed to the formation of a durable oxide surface layer analogous to the titanium oxide layer that inhibits body fluid reaction to titanium nickel alloys, and/or the non-existence of crystal domain boundaries may inhibit corrosive chemical attack. Methods for controlling the formation of the protective aluminum oxide layer are also described, as are devices including such biocompatible single crystal copper-based SMAs.

12 Claims, 26 Drawing Sheets

(56) References Cited

U.S. PATENT DOCUMENTS

| | | |
|---|---|---|
| 2,647,017 A | 7/1953 | Coulliette |
| 2,793,036 A | 5/1957 | Hansburg |
| 2,911,504 A | 11/1959 | Cohn |
| 3,229,956 A | 1/1966 | White |
| 3,351,463 A | 11/1967 | Rozner et al. |
| 3,357,432 A | 12/1967 | Sparks |
| 3,400,906 A | 9/1968 | Stocklin |
| 3,408,890 A | 11/1968 | Bochman, Jr. |
| 3,435,823 A | 4/1969 | Edwards |
| 3,445,086 A | 5/1969 | Quinn |
| 3,454,286 A | 7/1969 | Anderson et al. |
| 3,546,996 A | 12/1970 | Grijalva et al. |
| 3,559,641 A | 2/1971 | Lay |
| 3,561,537 A | 2/1971 | Dix et al. |
| 3,613,732 A | 10/1971 | Willson et al. |
| 3,620,212 A | 11/1971 | Fannon, Jr. et al. |
| 3,659,625 A | 5/1972 | Coiner et al. |
| 3,725,835 A | 4/1973 | Hopkins et al. |
| 3,789,838 A | 2/1974 | Fournier et al. |
| 3,849,756 A | 11/1974 | Hickling |
| 3,888,975 A | 6/1975 | Ramwell |
| 3,913,572 A | 10/1975 | Wheeler |
| 3,918,443 A | 11/1975 | Vennard et al. |
| 3,974,844 A | 8/1976 | Pimentel |
| 4,055,955 A | 11/1977 | Johnson |
| 4,063,831 A | 12/1977 | Meuret |
| 4,072,159 A | 2/1978 | Kurosawa |
| 4,096,993 A | 6/1978 | Behr |
| 4,145,764 A * | 3/1979 | Suzuki et al. ............... 427/2.27 |
| 4,151,064 A | 4/1979 | Kuehnle |
| 4,176,719 A | 12/1979 | Bray |
| 4,177,327 A | 12/1979 | Mathews |
| 4,243,963 A | 1/1981 | Jameel et al. |
| 4,265,684 A | 5/1981 | Boll |
| 4,279,190 A | 7/1981 | Hummel |
| 4,279,790 A | 7/1981 | Nakajima |
| 4,340,049 A | 7/1982 | Munsch |
| 4,434,855 A | 3/1984 | Given, Jr. |
| 4,485,545 A | 12/1984 | Caverly |
| 4,501,058 A | 2/1985 | Schutzler |
| 4,524,343 A | 6/1985 | Morgan et al. |
| 4,549,717 A | 10/1985 | Dewaegheneire |
| 4,551,974 A | 11/1985 | Yaeger et al. |
| 4,553,393 A | 11/1985 | Ruoff |
| 4,558,715 A | 12/1985 | Walton et al. |
| 4,567,549 A | 1/1986 | Lemme |
| 4,585,209 A | 4/1986 | Aine et al. |
| 4,589,179 A | 5/1986 | Hulting, Jr. |
| 4,596,483 A | 6/1986 | Gabriel |
| 4,619,284 A | 10/1986 | Delarue et al. |
| 4,654,191 A | 3/1987 | Krieg |
| 4,684,913 A | 8/1987 | Yaeger |
| 4,706,758 A | 11/1987 | Johnson |
| 4,753,465 A | 6/1988 | Dalby |
| 4,821,997 A | 4/1989 | Zdeblick |
| 4,823,607 A | 4/1989 | Howe et al. |
| 4,824,073 A | 4/1989 | Zdeblick |
| 4,848,388 A | 7/1989 | Waldbusser |
| 4,854,797 A | 8/1989 | Gourd |
| 4,864,824 A | 9/1989 | Gabriel et al. |
| 4,893,655 A | 1/1990 | Anderson |
| 4,896,728 A | 1/1990 | Wolff et al. |
| 4,915,773 A | 4/1990 | Kravetsky et al. |
| 4,943,032 A | 7/1990 | Zdeblick |
| 5,044,947 A | 9/1991 | Sachdeva et al. |
| 5,060,888 A | 10/1991 | Vezain et al. |
| 5,061,137 A | 10/1991 | Gourd |
| 5,061,914 A | 10/1991 | Busch et al. |
| 5,069,419 A | 12/1991 | Jerman |
| 5,072,288 A | 12/1991 | MacDonald et al. |
| 5,102,276 A | 4/1992 | Gourd |
| 5,114,504 A | 5/1992 | AbuJudom, II et al. |
| 5,116,252 A | 5/1992 | Hartman |
| 5,117,916 A | 6/1992 | Ohta et al. |
| 5,119,555 A | 6/1992 | Johnson |
| 5,129,753 A | 7/1992 | Wesley et al. |
| 5,131,843 A | 7/1992 | Hilgers et al. |
| 5,160,233 A | 11/1992 | McKinnis |
| 5,190,546 A | 3/1993 | Jervis |
| 5,192,147 A | 3/1993 | McCloskey |
| 5,211,371 A | 5/1993 | Coffee |
| 5,218,998 A | 6/1993 | Bakken et al. |
| 5,245,738 A | 9/1993 | Johnson |
| 5,309,717 A | 5/1994 | Minch |
| 5,312,152 A | 5/1994 | Woebkenberg, Jr. et al. |
| 5,312,247 A | 5/1994 | Sachdeva et al. |
| 5,325,880 A | 7/1994 | Johnson et al. |
| 5,344,117 A | 9/1994 | Trah et al. |
| 5,364,046 A | 11/1994 | Dobbs et al. |
| 5,395,238 A | 3/1995 | Andreiko et al. |
| 5,447,432 A | 9/1995 | Andreiko et al. |
| 5,456,600 A | 10/1995 | Andreiko et al. |
| 5,474,448 A | 12/1995 | Andreiko et al. |
| 5,494,113 A | 2/1996 | Polan |
| 5,502,982 A | 4/1996 | Venetucci |
| 5,543,349 A | 8/1996 | Kurtz et al. |
| 5,605,543 A | 2/1997 | Swanson |
| 5,619,177 A | 4/1997 | Johnson et al. |
| 5,622,225 A | 4/1997 | Sundholm |
| 5,640,217 A | 6/1997 | Hautcoeur et al. |
| 5,641,364 A | 6/1997 | Golberg et al. |
| 5,645,423 A | 7/1997 | Collins, Jr. |
| 5,658,515 A | 8/1997 | Lee et al. |
| 5,676,356 A | 10/1997 | Ekonen et al. |
| 5,683,245 A | 11/1997 | Sachdeva et al. |
| 5,695,504 A | 12/1997 | Gifford, III et al. |
| 5,714,690 A | 2/1998 | Burns et al. |
| 5,722,989 A | 3/1998 | Fitch et al. |
| 5,771,742 A | 6/1998 | Bokaie et al. |
| 5,772,378 A | 6/1998 | Keto-Tokoi |
| 5,796,152 A | 8/1998 | Carr et al. |
| 5,819,749 A | 10/1998 | Lee et al. |
| 5,825,275 A | 10/1998 | Wuttig et al. |
| 5,837,394 A | 11/1998 | Schumm, Jr. |
| 5,840,199 A | 11/1998 | Warren |
| 5,850,837 A | 12/1998 | Shiroyama et al. |
| 5,867,302 A | 2/1999 | Fleming |
| 5,903,099 A | 5/1999 | Johnson et al. |
| 5,916,178 A | 6/1999 | Noone et al. |
| 5,924,492 A | 7/1999 | Kikuchi et al. |
| 5,930,651 A | 7/1999 | Terasawa |
| 5,960,812 A | 10/1999 | Johnson |
| 6,042,374 A | 3/2000 | Farzin-Nia et al. |
| 6,042,553 A | 3/2000 | Solar et al. |
| 6,072,617 A | 6/2000 | Henck |
| 6,073,700 A | 6/2000 | Tsuji et al. |
| 6,075,239 A | 6/2000 | Aksyuk et al. |
| 6,080,160 A | 6/2000 | Chen |
| 6,084,849 A | 7/2000 | Durig et al. |
| 6,101,164 A | 8/2000 | Kado et al. |
| 6,110,204 A | 8/2000 | Lazarov et al. |
| 6,123,153 A | 9/2000 | Finnegan |
| 6,124,523 A | 9/2000 | Banas et al. |
| 6,126,371 A | 10/2000 | McCloskey |
| 6,129,153 A | 10/2000 | Joung |
| 6,139,143 A | 10/2000 | Brune et al. |
| 6,195,478 B1 | 2/2001 | Fouquet |
| 6,203,715 B1 | 3/2001 | Kim et al. |
| 6,229,640 B1 | 5/2001 | Zhang |
| 6,247,493 B1 | 6/2001 | Henderson |
| 6,277,133 B1 | 8/2001 | Kanesaka |
| 6,284,067 B1 | 9/2001 | Schwartz et al. |
| 6,352,494 B2 | 3/2002 | McAlonan |
| 6,358,380 B1 | 3/2002 | Mann et al. |
| 6,386,507 B2 | 5/2002 | Dhuler et al. |
| 6,406,605 B1 | 6/2002 | Moles |
| 6,407,478 B1 | 6/2002 | Wood et al. |
| 6,410,360 B1 | 6/2002 | Steenberge |
| 6,447,478 B1 | 9/2002 | Maynard |
| 6,451,668 B1 | 9/2002 | Neumeier et al. |
| 6,454,913 B1 | 9/2002 | Rasmussen et al. |
| 6,470,108 B1 | 10/2002 | Johnson |
| 6,475,261 B1 | 11/2002 | Matsumoto et al. |
| 6,524,322 B1 | 2/2003 | Berreklouw |

(56) References Cited

U.S. PATENT DOCUMENTS

| | | | |
|---|---|---|---|
| 6,533,905 B2 | 3/2003 | Johnson et al. |
| 6,537,310 B1 | 3/2003 | Palmaz et al. |
| 6,582,985 B2 | 6/2003 | Cabuz et al. |
| 6,592,724 B1 | 7/2003 | Rasmussen et al. |
| 6,596,102 B2 | 7/2003 | Homma |
| 6,605,111 B2 | 8/2003 | Bose et al. |
| 6,614,570 B2 | 9/2003 | Johnson et al. |
| 6,620,634 B2 | 9/2003 | Johnson et al. |
| 6,624,730 B2 | 9/2003 | Johnson et al. |
| 6,669,794 B1 | 12/2003 | Bellouard et al. |
| 6,669,795 B2 | 12/2003 | Johnson et al. |
| 6,672,502 B1 | 1/2004 | Paul et al. |
| 6,688,828 B1 | 2/2004 | Post |
| 6,729,599 B2 | 5/2004 | Johnson |
| 6,742,761 B2 | 6/2004 | Johnson et al. |
| 6,746,890 B2 | 6/2004 | Gupta et al. |
| 6,771,445 B1 | 8/2004 | Hamann et al. |
| 6,790,298 B2 | 9/2004 | Johnson et al. |
| 6,811,910 B2 | 11/2004 | Tsai et al. |
| 6,840,329 B2 | 1/2005 | Kikuchi et al. |
| 6,843,465 B1 | 1/2005 | Scott |
| 6,852,132 B1 | 2/2005 | Houser et al. |
| 6,908,275 B2 | 6/2005 | Nelson et al. |
| 6,918,545 B2 | 7/2005 | Franson et al. |
| 6,920,966 B2 | 7/2005 | Buchele et al. |
| 6,955,187 B1 | 10/2005 | Johnson |
| 7,022,173 B2 * | 4/2006 | Cummings et al. ............ 264/16 |
| 7,040,323 B1 | 5/2006 | Menchaca et al. |
| 7,044,596 B2 | 5/2006 | Park |
| 7,073,504 B2 | 7/2006 | Callister et al. |
| 7,084,726 B2 | 8/2006 | Gupta et al. |
| 7,201,367 B2 | 4/2007 | Wietharn |
| 7,422,403 B1 | 9/2008 | Johnson et al. |
| 7,441,888 B1 | 10/2008 | Johnson |
| 7,736,687 B2 | 6/2010 | Sims et al. |
| 7,793,911 B2 | 9/2010 | Fontana et al. |
| 2001/0023010 A1 | 9/2001 | Yamada et al. |
| 2002/0018325 A1 | 2/2002 | Nakatani et al. |
| 2002/0062154 A1 | 5/2002 | Ayers |
| 2002/0106614 A1 | 8/2002 | Prince et al. |
| 2002/0192617 A1 | 12/2002 | Phan et al. |
| 2003/0002994 A1 | 1/2003 | Johnson et al. |
| 2003/0078465 A1 | 4/2003 | Pai et al. |
| 2003/0170130 A1 | 9/2003 | Johnson |
| 2004/0083006 A1 | 4/2004 | Ellingsen |
| 2004/0200551 A1 | 10/2004 | Brhel et al. |
| 2004/0221614 A1 | 11/2004 | Holemans et al. |
| 2004/0243219 A1 | 12/2004 | Fischer et al. |
| 2004/0249399 A1 | 12/2004 | Cinquin et al. |
| 2005/0113933 A1 | 5/2005 | Carter et al. |
| 2006/0118210 A1 | 6/2006 | Johnson |
| 2006/0204738 A1 | 9/2006 | Dubrow et al. |
| 2006/0213522 A1 | 9/2006 | Menchaca et al. |
| 2006/0232374 A1 | 10/2006 | Johnson |
| 2006/0240953 A1 | 10/2006 | Shahinpoor |
| 2007/0137740 A1 | 6/2007 | Johnson et al. |
| 2007/0207321 A1 | 9/2007 | Abe et al. |
| 2007/0246233 A1 | 10/2007 | Johnson |
| 2008/0075557 A1 | 3/2008 | Johnson et al. |
| 2008/0213062 A1 | 9/2008 | Johnson |
| 2009/0035859 A1 | 2/2009 | Johnson |
| 2009/0183986 A1 | 7/2009 | Johnson et al. |
| 2010/0129766 A1 | 5/2010 | Hilgers |
| 2010/0190127 A1 | 7/2010 | Ghantiwala et al. |

FOREIGN PATENT DOCUMENTS

| | | |
|---|---|---|
| EP | 1122526 | 8/2001 |
| EP | 1238600 | 9/2002 |
| GB | 2187951 | 9/1987 |
| JP | 57161031 | 10/1982 |
| JP | 58088200 A | 5/1983 |
| JP | 59179771 | 10/1984 |
| JP | 07090624 | 4/1995 |
| JP | 10173306 | 6/1998 |
| JP | 2000185999 A | 7/2000 |
| SU | 1434314 | 10/1988 |
| WO | WO98/53362 | 11/1998 |
| WO | WO99/16387 A1 | 4/1999 |
| WO | WO99/62432 | 12/1999 |
| WO | WO00/04204 | 1/2000 |
| WO | WO03/052150 | 6/2003 |
| WO | WO2005/108635 | 11/2005 |
| WO | WO2006/019943 | 2/2006 |

OTHER PUBLICATIONS

Brice et al.; Crystal Growth; Ullmann's Encyclopedia of Industrial Chemistry; 2007; Wiley-VCH Verlag GmBH; pp. 1, 29-42, 50.

Buchaillot et al., "Thin film of titanium/nickel shape memory alloy for multi-degree of freedom microactuators", Seisan Kenkyu, vol. 51, No. 8, 1999, pp. 22-23.

ElastametTM brochure from New Discovery Metals; 2007.

ElastametTM website screen capture, accessed Jul. 23, 2008.

Fu et al.; The growth characteristics with a shape memory effect; J. Phys.: Condens. Matter; vol. 4; 1992; pp. 8303-8310.

Johnson et al., "Application of shape memory alloys: advantages, disadvantages, and limitations," Micromachining and Microfabrication Process Technology VII, 22-4, Oct. 2001, San Francisco, CA, USA, vol. 4557, pp. 341-351.

Martynov, V., "TiNi thin films for microactuators and microdevices: sputter deposition and processing techniques", Thermec' 2003, Internat'l Conf. on Processing and Manufacturing of Advanced Materials, Jul. 7-11, 2003, Leganes, Madrid, Spain, Materials Science Forum, Jul. 7, 2003 vol. 426-432; pp. 3475-3480.

Morgan; Medical shape memory alloy applications—the market and its products; Materials Science and engineering A 378; 2004; pp. 16-23.

Nelson, Lewis S.; Copper; Goldfrank's Toxicologic Emergencies (7th Ed.); McGraw-Hill; Chap. 82C; pp. 1262-1271; 2002.

Pauling, Linus, College Chemistry, second edition, W.H. Freeman and Company, San Francisco, 1955, pp. 81-91.

Qingfu et al.; Stabilisation of martensite during training of Cu-Al-Ni single crystals; Journal de Physique IV; Collloqu C2; Supplement to the Journa de Physique III; vol. 5; Feb. 1995; pp. 181-186.

Recarte et al.; Influence of Al and Ni concentration on the martensitic transformation in Cu-Al-Ni shape-memory alloys; Metallurgical and MaterialsTransactions A; vol. 33A; Aug. 2002; pp. 2581-2591.

Sittner et al.; Stress induced martensitic transformations in tension/torsion of CuAlNi single crystal tube; Scripta Materialia; vol. 48; 2003; pp. 1153-1159.

Sutuo et al.; Development of medical guide wire of Cu-Al-Mn-base superelastic alloy with functionally graded characteristics; Mater Res Part B: Appl Biomater; vol. 69B; 2004; pp. 64-69.

Takabayashi et al., "Reversible shape memory alloy film fabricated by RF sputtering", Materials and Manufacturing Processes, vol. 13, No. 2, 1998, pp. 275-286.

Viahhi et al.; "Robototechnic Constructions Based on CU-AL-NI Single Crystal Actuators;" Proceedings of Second International Conference on Shape Memory and Superelastic Technologies; 1997; United States.

Wang et al.; Temperature memory effect in CuAlNi single crystalline and CUZnAl polycrystalline shape memory alloys; Thermochimica Acta; vol. 448; 2006; pp. 69-72.

Yahia et al.; Bioperformance of shape memory alloy single crystals; Bio-Medical Materials and Engineering; vol. 16; 2006; pp. 101-118.

Zhang et al.; Nanoscale pseudoelasticity of single-crystal Cu-Al-Ni shape-memory alloy induced by cyclic nanoindentation; J Mater Sci; vol. 41; 2006; pp. 5021-5024.

Zhang et al.; The variant selection criteria in single-crystal CuAlNi shape memory alloys; Smart Mater. Struct.; vol. 9; 2000; pp. 571-581.

Zhdanov et al.; Thermal stresses in tubes, produced from a melt by the Stepanov method, during their cooling; Journal of Engineering Physics and Thermophysics; vol. 68; No. 1; 1995; pp. 80-89.

Xiaogdang, Ma; U.S. Appl. No. 10/972,759 entitled "Magnetic data storage system," filed Oct. 25, 2004.

(56) References Cited

OTHER PUBLICATIONS

Johnson, David et al.; U.S. Appl. No. 11/006,501 entitled "Anastomosis device and method," filed Dec. 6, 2004.

Johnson, David et al.; U.S. Appl. No. 11/041,185 entitled "Single crystal shape memory alloy devices and methods," filed Jan. 24, 2005.

Johnson, David; U.S. Appl. No. 11/420,157 entitled "Shape memory allow thin film, method of fabrication, and articles of manufacture," filed May 24, 2006.

Johnson, David et al.; U.S. Appl. No. 11/948,852 entitled "Method of alloying reactive elemental components," filed Nov. 30, 2007.

Johnson, David et al.; U.S. Appl. No. 11/949,663 entitled "Hyperelastic shape setting devices and fabrication methods," filed Dec. 3, 2007.

Johnson et al.; U.S. Appl. No. 12/019,553 entitled "Frangible shape memory alloy fire sprinkler valve actuator," filed Jan. 24, 2008.

http://www.algor.com/news_pub/tech_reports/2005/rubber&foam/default.asp.

Christian et al.; The application of shape memory actuators in anthropomorphic upper limb prostheses; Artif. Organs; vol. 27; No. 5; pp. 473-477; 2003.

Dario et al.; Shape memory alloy microactuators for minimal invasive surgery; Proceedings of SMST-94 Conference; pp. 427-433; Pacific Grove CA; 1994.

Johnson, A. D.; Vacuum-deposited TiNi shape memory film: Characterization and applications in microdevices; J. Micromech. Microeng.; vol. 1; pp. 34-41; 1991.

Krulevitch et al.; Thin film shape memory alloy microactuators; J. Micromech. Microeng.; vol. 5; No. 4; pgs. 26; 1996.

Schetky, L.M.; Shape-memory alloys; Scientific American, pp. 74-82; 1979.

Johnson et al.; U.S. Appl. No. 12/503,614 entitled "Sprinkler valve with active actuation," filed Jul. 15, 2009.

Johnson, A. David; U.S. Appl. No. 12/952,002 entitled "Hyperelastic shape setting devices and fabrication methods," filed Nov. 22, 2010.

Creuziger et al.; Initial transformation around a notch tip in CuAlNi: experiment and modeling; Acta Materialia; vol. 56; pp. 518-526; 2008.

Gill et al.; Three-Dimensional Thin-Film Shape Memory Alloy Microactuator With Two-Way Effect; Journal of Microelectromechanical Sys.; vol. 11; No. 1; pp. 68-77; Feb. 2002.

Johnson, Alfred D.; U.S. Appl. No. 13/220,522 entitled "Method and devices for preventing restenosis in cardiovascular stents," filed Aug. 29, 2011.

Johnson et al.; U.S. Appl. No. 13/215,438 entitled "Shape setting a shape memory alloy dental arch," filed Aug. 23, 2011.

* cited by examiner

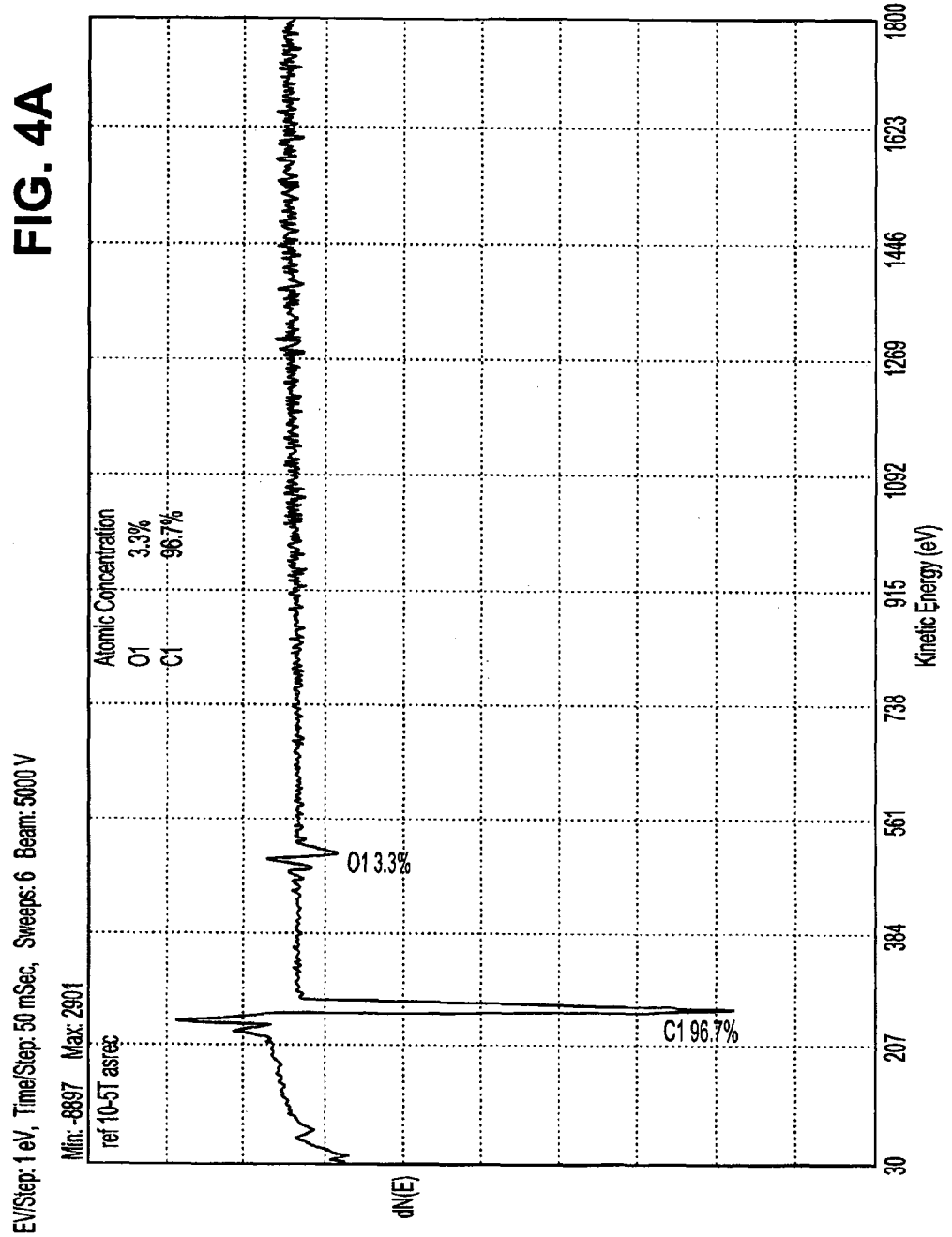

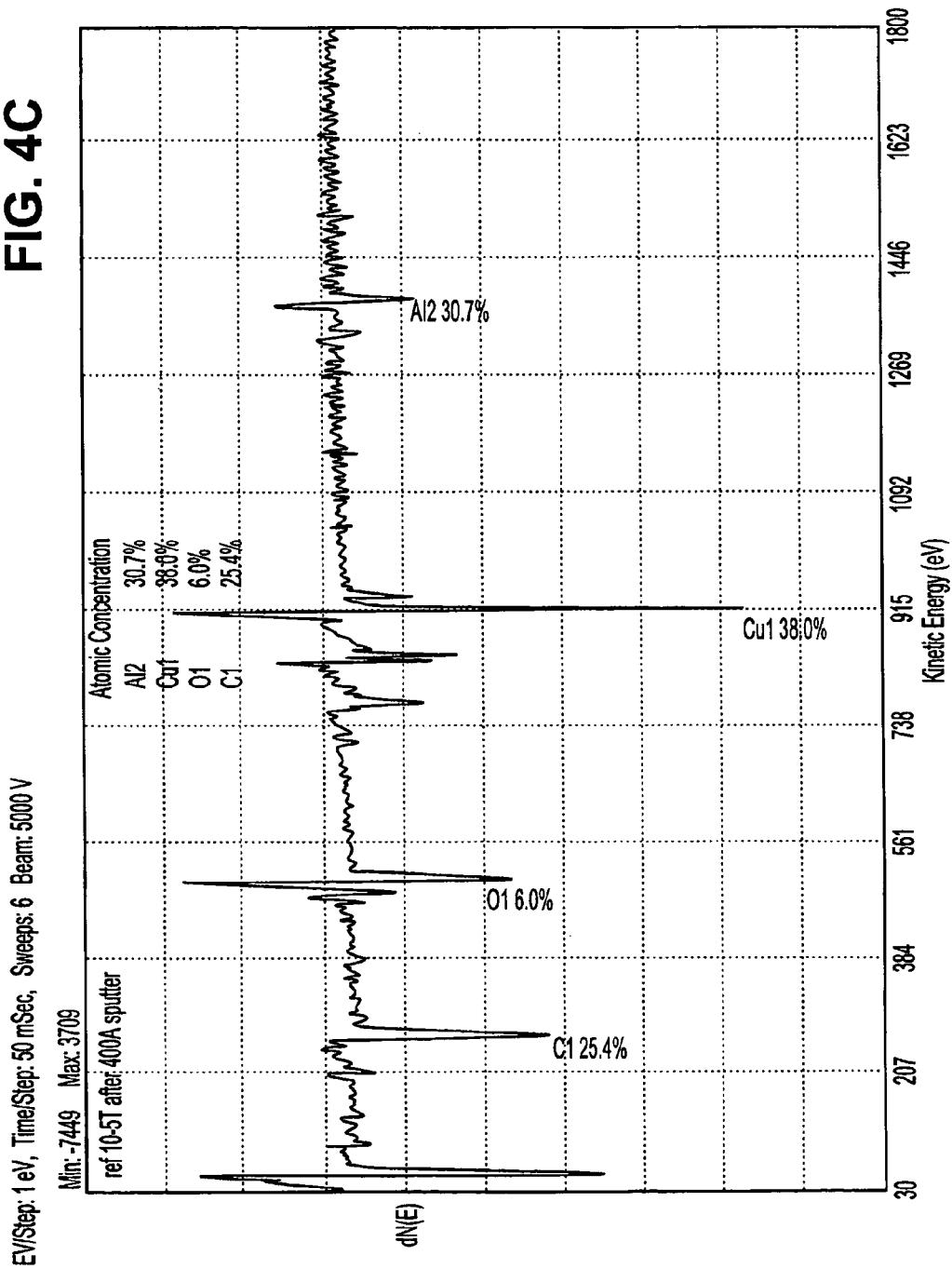

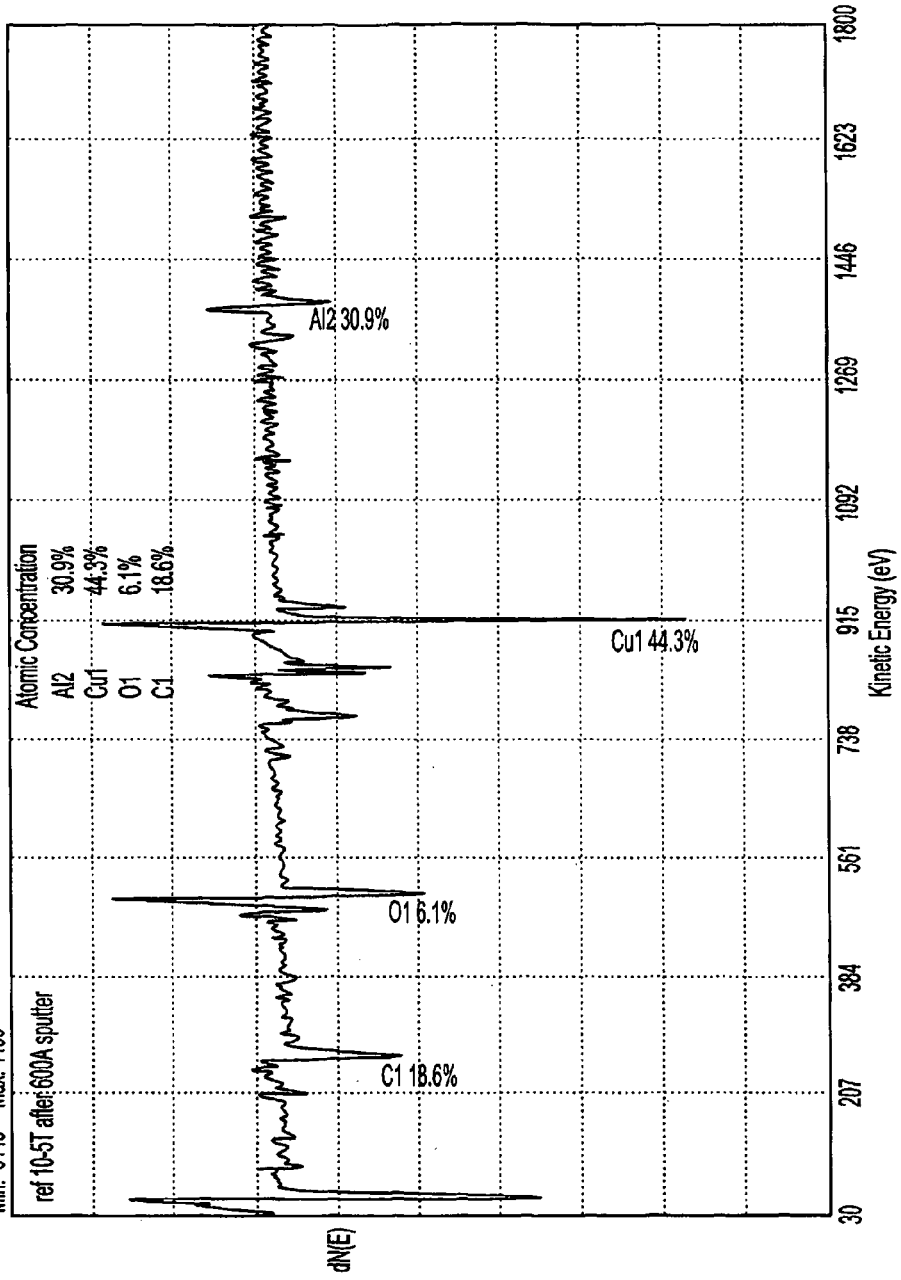

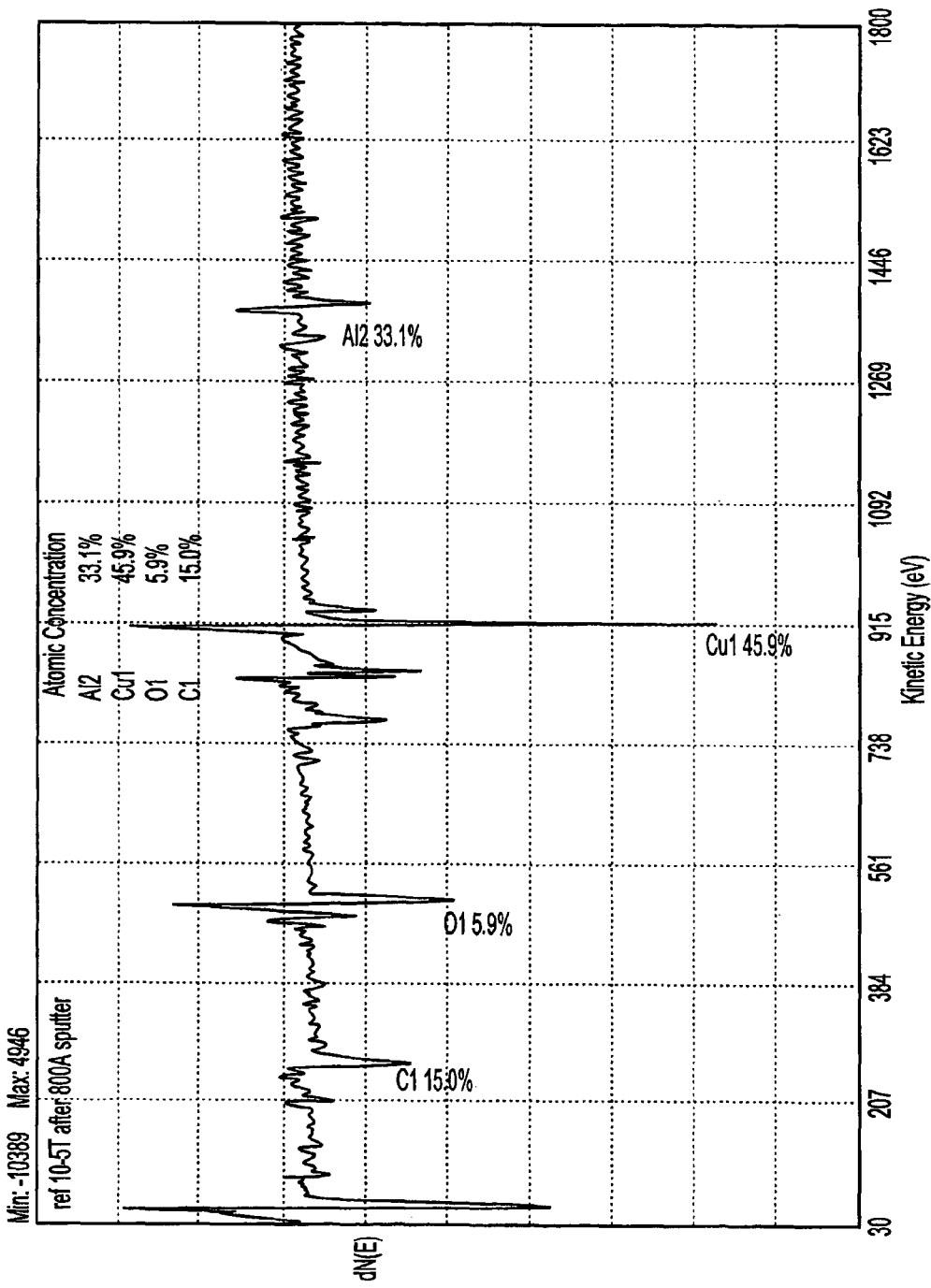

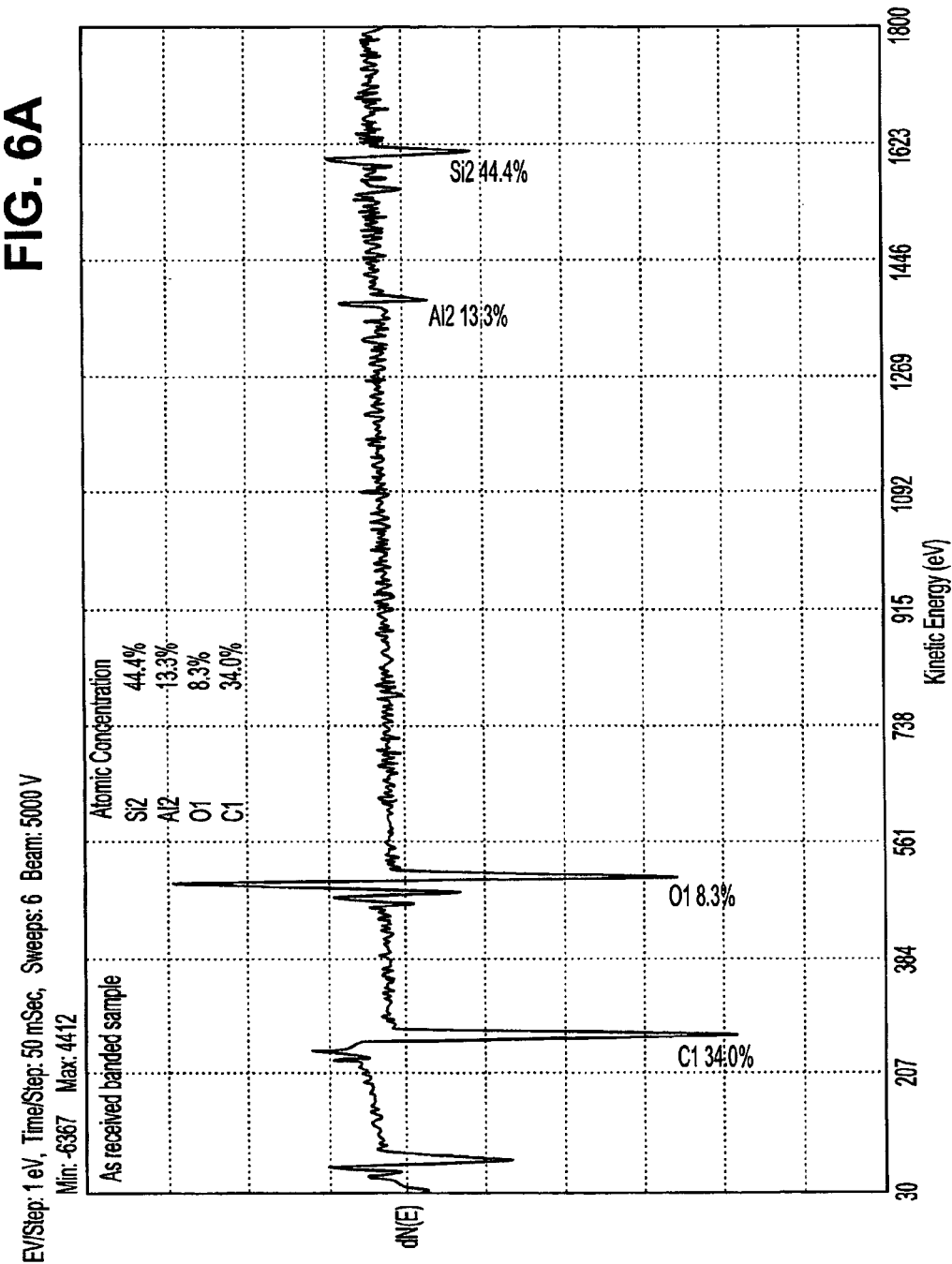

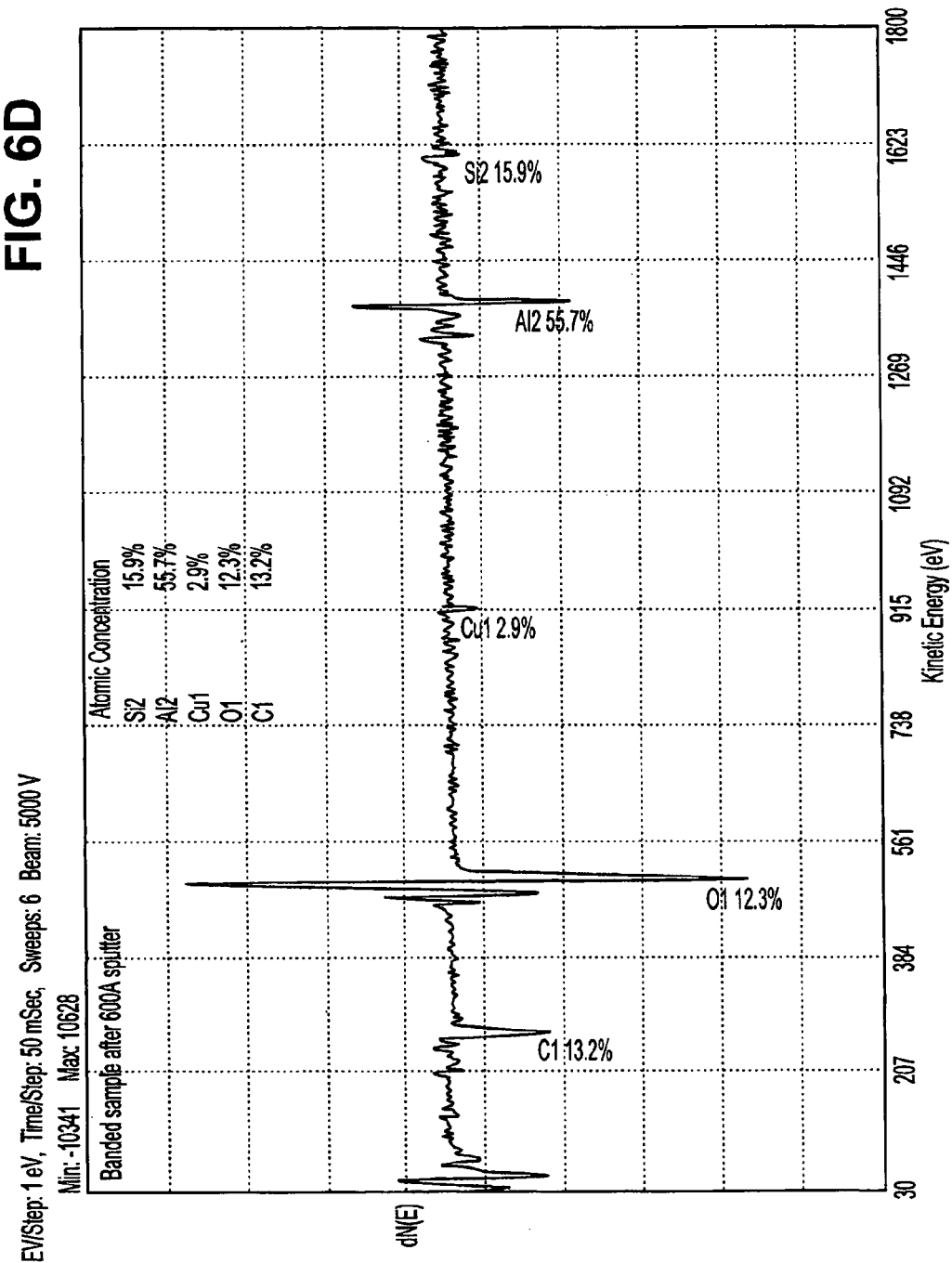

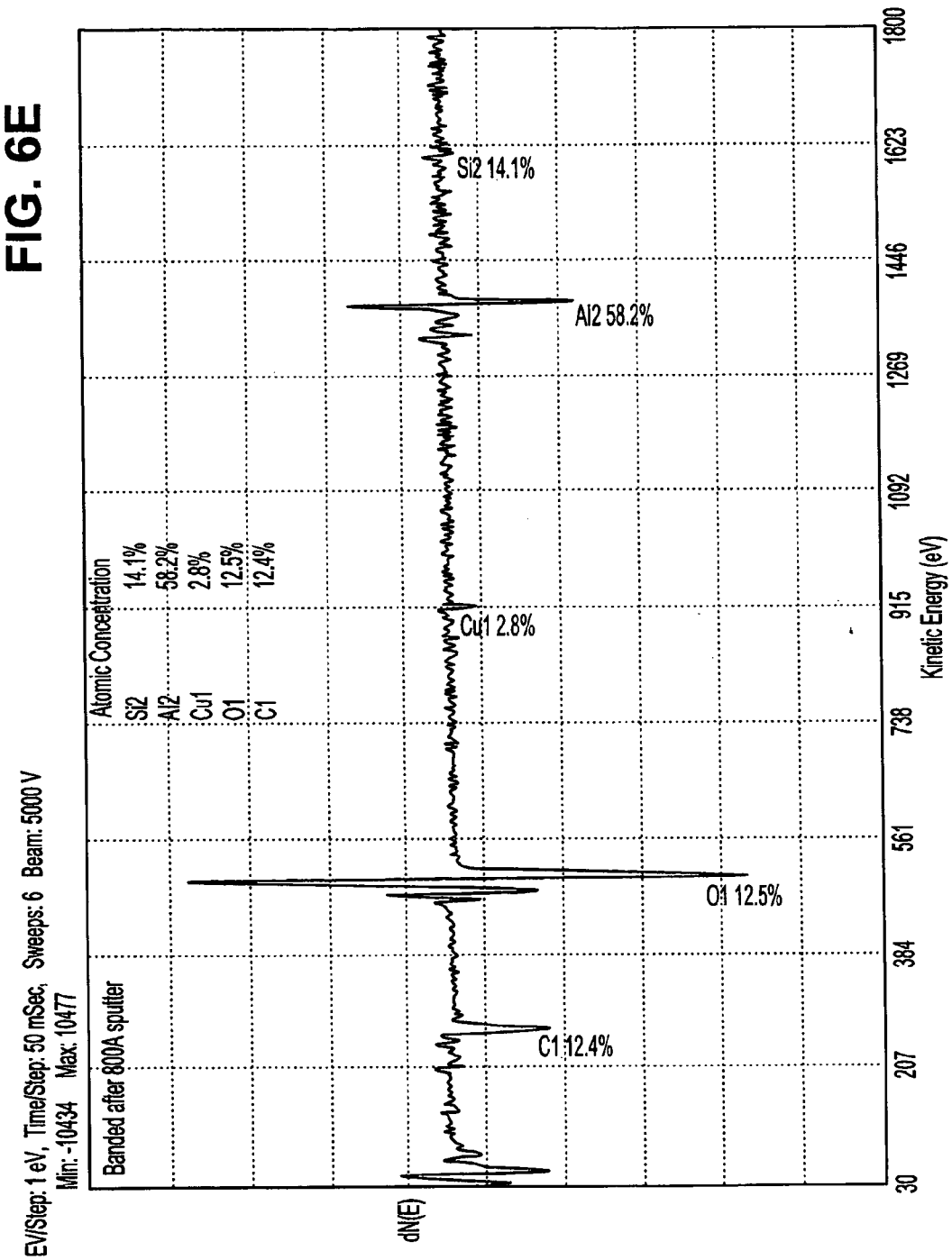

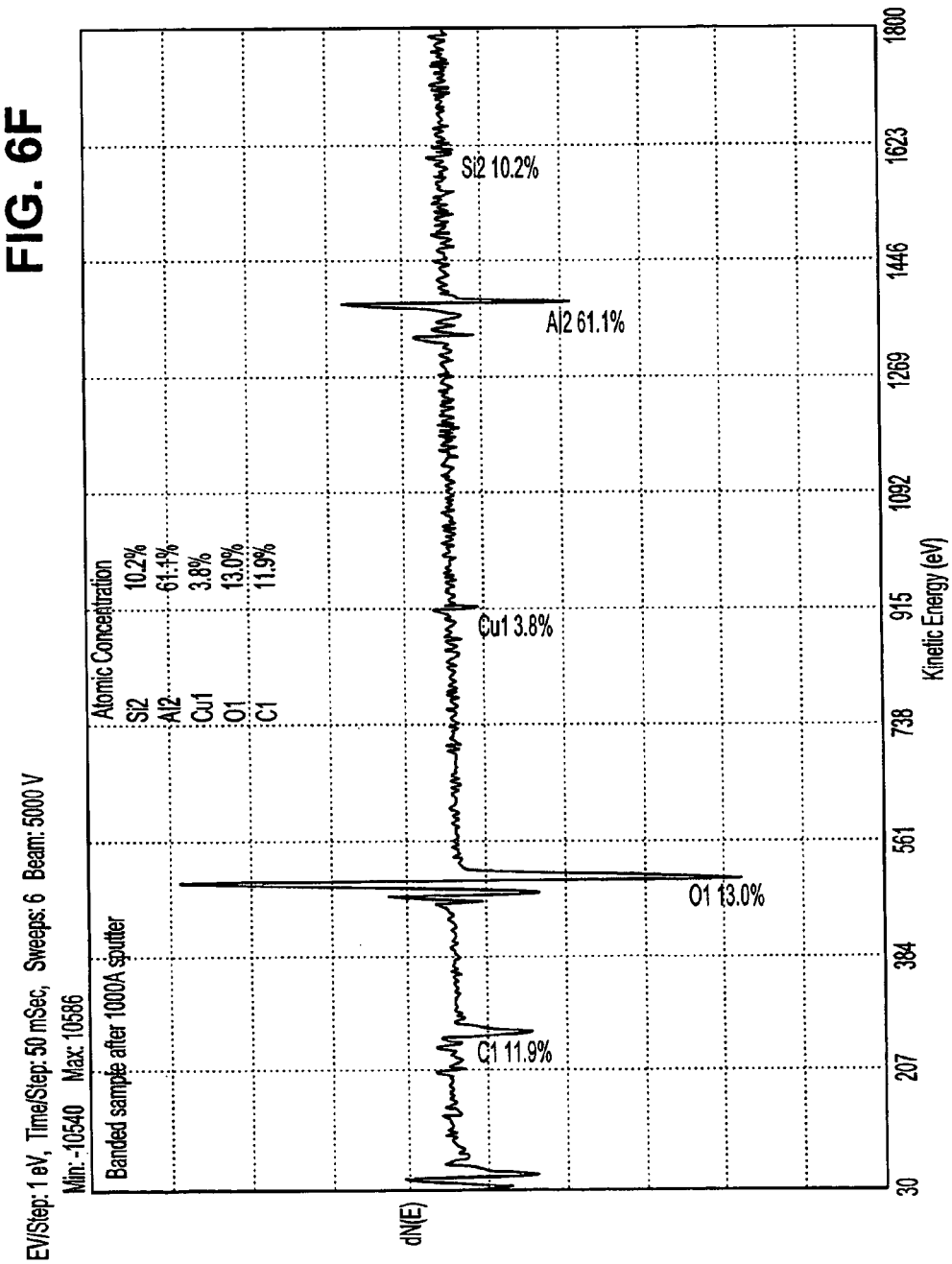

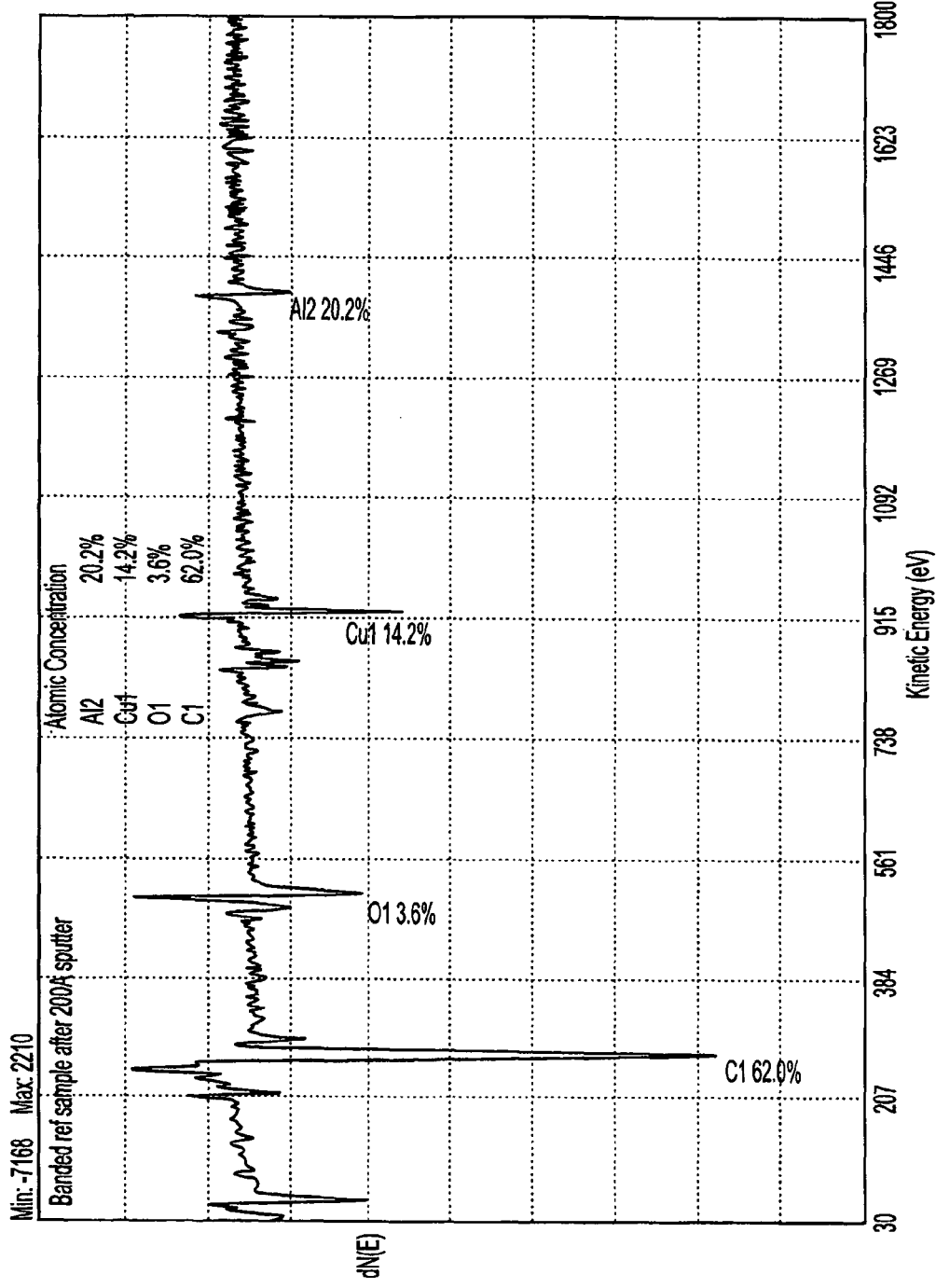

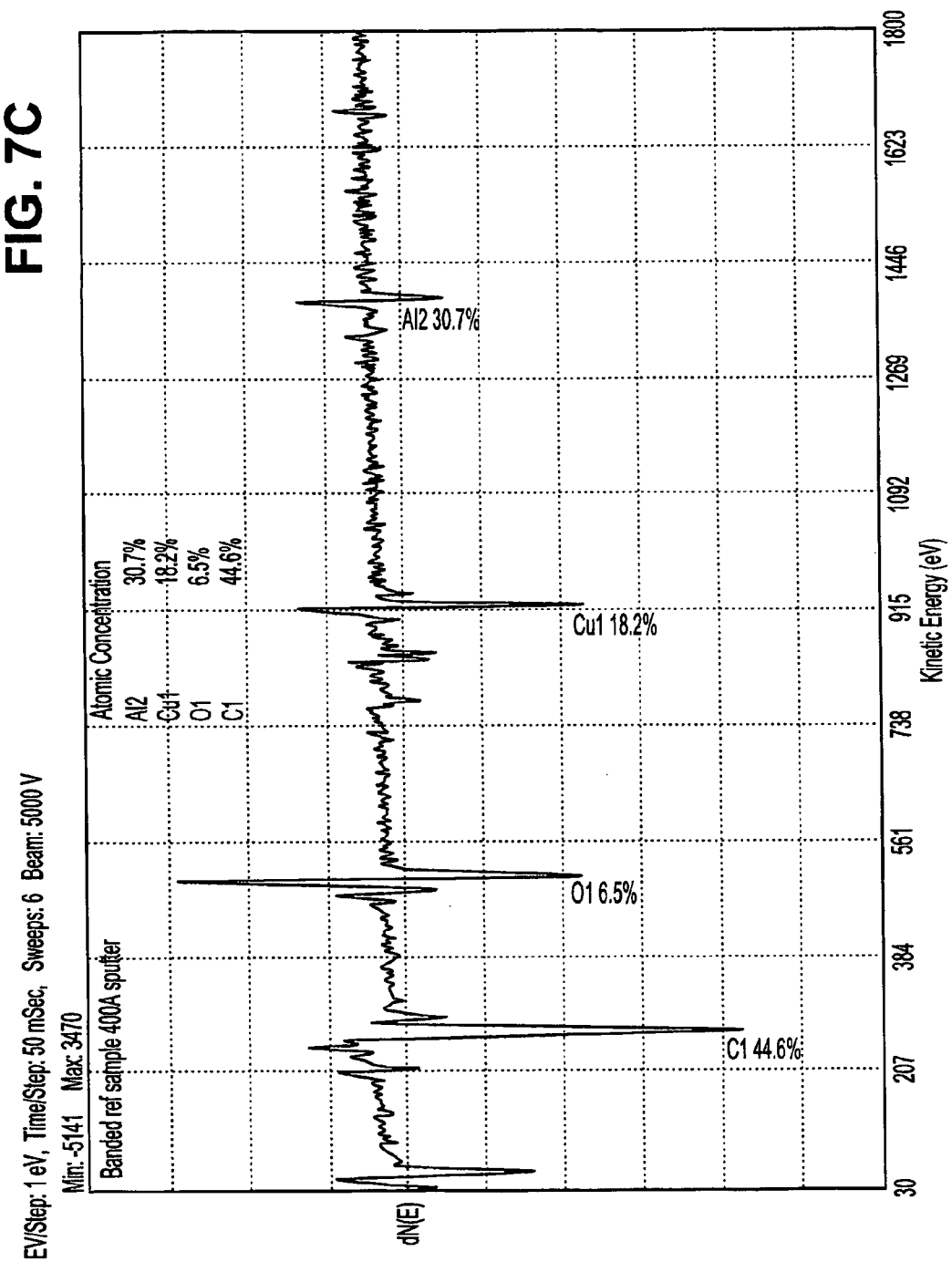

BIOCOMPATIBLE COPPER-BASED SINGLE-CRYSTAL SHAPE MEMORY ALLOYS

CROSS-REFERENCE TO RELATED APPLICATION

This application claims the benefit under 35 U.S.C. 119 of U.S. Provisional Patent Application No. 60/991,634 filed Nov. 30, 2007, titled "BIOCOMPATIBLE COPPER-BASED SINGLE-CRYSTAL SHAPE MEMORY ALLOYS".

STATEMENT AS TO FEDERALLY SPONSORED RESEARCH

This invention was made with the support of the United States government under DARPA Contract number W31P4Q-05-C-0158.

BACKGROUND OF THE INVENTION

1. Field of the Invention

The invention is directed to an improved method of making and using copper-based single crystal shape memory alloys (SMAs). In particular, this invention is directed to SMAs of CuAlNi that are biocompatible.

2. Background

Certain SMAs are used in medical devices, including implants. In particular, nickel titanium SMAs such as "Nitinol" have become widely known as a biocompatible shape memory alloy. Nitinol is a compound of nickel and titanium, and has become used extensively in medical and similar applications because it is more flexible than steel. Another class of SMAs, the copper-aluminum-nickel superelastic alloys also exhibit large shape recovery and would be useful in medical devices were it not for the widespread belief that their large copper content is cytotoxic, and would result in deleterious interaction with living tissue, particularly in long-term embodiments.

SMAs including copper are believed to be cytotoxic because copper is widely accepted as a cytotoxic metal. Copper is among the more frequently reported metals with which patients are poisoned, and routinely ranks third (behind lead and arsenic) in non-medicinal metal exposures reported to US Poison Control Centers. See, e.g., *Goldfrank's Toxicologic Emergencies* (7$^{th}$ Edition), Chapter 82C, "Copper," by Lewis S. Nelson (2002: McGraw-Hill).

The cytotoxicity of copper-based shape memory alloys, and particularly single-crystal copper-based shape memory alloys is well documented. The prior art generally teaches away from using exposed single-crystal Cu-based alloys because of this presumed cytotoxicity. For example, Yahia et al. (Yahia, Manceur, and Chaffraix, "Bioperformance of shape memory alloy single crystals", Bio-Medical Materials and Engineering 16:101-118 (2006)) discusses the presumed cytotoxicity of copper-based single-crystal alloys. Even as recently as 2008, copper-based single-crystal alloys are presumed to be cytotoxic. For example, Creuziger and Crone, ("Initial transformation around a notch tip in CuAlNi: Experiment and modeling," Acta Materialia, (2008) 56:518-526).

However, copper-based SMAs may be extremely useful. Superelastic single crystal CuAlNi is extraordinarily flexible, even compared to other SMAs (e.g., Ti-Ni alloys and Fe-based alloys). In particular, single crystal CuAlNi alloys may have properties that are highly desirable. For example, a single crystal CuAlNi material may have a strain-recovery that is nearly 10percent strain, which can be described as 'hyperelastic' (hyperelastic behavior is described in U.S. patent application Ser. No. 10/588,413, herein incorporated by reference in its entirety). Thus, while shape memory alloys transform from one solid crystal structure to another, and are capable of energy storage at greater densities than elastic materials, in hyperelastic transformations, the energy is absorbed and released at nearly constant force, so that constant acceleration is attainable. Many medical procedures would benefit from improved flexibility, for example, archwires for orthodontistry, guidewires for catheters, and clot retrievers for intracranial and cardiovascular intervention. However, each of these applications requires material that can be exposed to tissues and/or the blood stream without causing toxic damage.

To date, however, virtually nothing is known about the biocompatibility of copper-based SMAs, beyond the assumption in the art that such materials are cytotoxic because of their high copper content, making them unsuitable for biological (e.g., implanted or chronic) use.

We show here that single-crystal copper-aluminum-nickel SMAs may be prepared so that they are biocompatible. Results of MEM elution cell cytotoxicity, ISO intramuscular implant, and hemo-compatibility tests were performed to show that CuAlNi alloys can be fully biocompatible. Copper-aluminum-nickel (or copper-aluminum manganese or beryllium) may be made biocompatible by the formation of a durable oxide surface layer analogous to the titanium oxide layer that inhibits body fluid reaction to titanium nickel alloys. The oxide layer may be made durable and capable of withstanding implantation or biological use.

SUMMARY OF THE INVENTION

Described herein are methods of forming biocompatible shape memory alloys (SMA). In general, these methods include forming a single crystal copper-based (e.g., copper-aluminum) shape memory alloy, and forming a controlled layer of aluminum oxide on the single crystal copper-based shape memory alloy.

In general, the controlled layer of aluminum oxide is actively applied or formed, in contrast to the thin, and likely irregular (accidental) layer of Aluminum oxide that may be formed. The controlled layer is formed by further modification of the single-crystal material (e.g., by controlling the concentration of Al near the outer surface, etc.).

The step of forming a single crystal copper-aluminum alloy typically includes lowering a seed of a copper aluminum based alloy into a molten melt of a copper aluminum based alloy, wherein the seed is aligned on the <100>crystallographic direction in a direction of pulling, pulling a column of the alloy of arbitrary length from the melt by pulling at a pulling rate so that the rising column is cooled relative to the melt, to form a crystallization front above the surface of the melt, wherein the melt is kept at a constant temperature and has a composition so that the pulled single crystal column has a transition temperature from martensite to austenite that is below 37 degrees Celsius, applying a predetermined hydrostatic pressure on the column and heating the column to a temperature less than 1100° C., the pulling rate, hydrostatic pressure and temperature being sufficient to crystallize the alloy in the column into a single crystal, and rapidly quenching the single crystal.

The step of forming the controlled layer of aluminum oxide may include doping the surface with Al after forming the single crystal of copper-based shape memory alloy. In some variations, the step of forming the controlled layer of aluminum oxide comprises anodizing the outer surface of the single crystal copper-based shape memory alloy. For example, the controlled layer of aluminum oxide may be formed by applying a high voltage to the single crystal copper-based shape memory alloy to form an aluminum oxide layer on the outer surface.

In some variations, the method of forming a biocompatible SMA includes applying a sealant to the outer surface of the single crystal copper-based shape memory alloy.

The formation of a biocompatible SMA may also include the step of polishing at least a portion of the outer surface of the single crystal copper-based shape memory alloy (e.g., by electropolishing, grinding, etc.).

The single crystal copper-based shape memory alloy may be formed in any appropriate manner. For example, US Patent application titled "METHOD OF ALLOYING REACTIVE COMPONENTS" to Johnson et al., claiming priority to U.S. provisional patent Application Ser. No. 60/868,116, titled "METHOD OF ALLOYING REACTIVE ELEMENTAL COMPOSITIONS," (filed on Dec. 1, 2006) describes exemplary methods of forming single crystal shape memory alloys.

In some variations, the single crystal copper-based shape memory alloy is a CuAlNi alloy.

Also described herein are methods of forming a biocompatible single crystal copper-based shape memory alloy including the steps of: forming a single crystal copper-based shape memory alloy; preparing the surface of the single crystal copper-based shape memory alloy; and forming a controlled layer of aluminum oxide on the single crystal copper-based shape memory alloy.

The step of preparing the surface of the single crystal copper-based shape memory alloy may include polishing or grinding the surface. In some variations, the step of preparing the surface includes etching the surface.

In some variations, the step of forming the controlled layer of aluminum oxide comprises doping the surface with Al after forming the single crystal of copper-based shape memory alloy, anodizing the outer surface of the single crystal copper-based shape memory alloy, and/or applying a high voltage to the single crystal copper-based shape memory alloy.

Also described herein are biocompatible devices for use within a body. These devices typically include a single crystal copper-based (e.g., copper aluminum) SMA having a protective outer layer of aluminum oxide. The single-crystal copper-based SMA may be, for example, CuAlNi. The protective outer layer of aluminum oxide may be an amorphous layer of aluminum oxide, or a substantially crystalline aluminum oxide. In some variations, the protective outer layer of aluminum oxide is greater than 10 nm thick, or greater than 100 nm thick, or greater than 500 nm thick. In some variations, the protective outer layer of aluminum oxide is approximately uniform in thickness. In some variations, the protective outer layer of aluminum oxide is non-uniform in thickness. For example, the protective outer layer of aluminum oxide is thicker in regions of the single crystal copper-based SMA having a larger or a smaller diameter.

The biocompatible devices including a single crystal copper-based SMA may be: a joint replacement, a hip bone replacement, a guidewire, a clot retriever, a blood filter, a stent, a dental arch, or virtually any other implantable device. Examples of these methods and devices are provided herein.

INCORPORATION BY REFERENCE

All publications and patent applications mentioned in this specification are herein incorporated by reference in their entirety to the same extent as if each individual publication or patent application was specifically and individually indicated to be incorporated by reference.

BRIEF DESCRIPTION OF THE DRAWINGS

FIGS. 4A-4F show Auger electron spectroscopy (AES) at the surface and at progressively deeper plasma-etched levels (in increments of 200Å, respectively) for a copper-based SMA.

FIGS. 6A-6F show Auger electron spectroscopy (AES) at the surface and at progressively deeper plasma-etched levels (in increments of 200Å, respectively) for a banded sample of copper-based SMA.

FIGS. 7A-7F show another set of Auger electron spectroscopy (AES) at the surface and at progressively deeper plasma-etched levels (in increments of 200Å, respectively) for a banded sample of copper-based SMA.

DETAILED DESCRIPTION OF THE INVENTION

Figure 1:
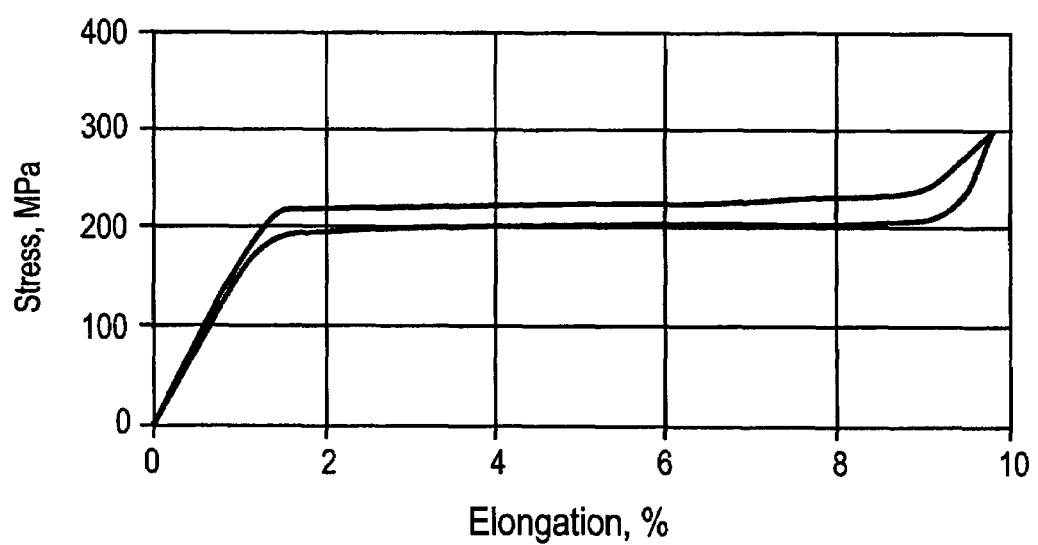
FIG. 1 shows the stress-strain profile for one variation of a hyperelastic SMA as described herein.

Articles made of single crystal copper-aluminum-nickel superelastic alloys exhibit large shape recovery and would be useful in medical devices were it not for the perception that their large copper content must cause deleterious interaction with living tissue.

We herein show that Cu-based SMAs can be biocompatible. In particular, we show the results of MEM elution cell cytotoxicity, ISO intramuscular implant, and hemo-compatibility tests producing negative cytotoxic results. This biocompatibility may be attributed to the formation of a durable oxide surface layer analogous to the titanium oxide layer that inhibits body fluid reaction to titanium nickel alloys. Furthermore (or alternatively), the non-existence of crystal domain boundaries may inhibit corrosive chemical attack. Experimental biocompatibility results, surface analysis, and suggested applications are discussed. We also describe methods for enhancing the biocompatibility of Copper-based SMAs for medical uses.

Copper-Based SMAs

Superelastic single crystal CuAlNi is extraordinarily flexible. Many procedures in medical practice that will benefit from improved flexibility, such as archwires for orthodontistry, guidewires for catheters, clot retrievers for intracranial and cardiovascular intervention, etc. Each of these applications requires material that can be exposed to tissues and/or the blood stream without causing toxic damage.

By comparison, Nitinol, a compound of nickel and titanium, is used extensively in these and similar applications because it is more flexible than steel. Single crystal superelastic CuAlNi can do what Nitinol wire can do, and with improvement: shape recovery is complete. See FIG. 1.

A material is biocompatible if it can be in contact with living body tissues for extended periods without thrombogenicity or corrosion. This may be alternatively expressed as the ability of a material to perform with an appropriate host response in a specific application (Williams' definition), or as the quality of not having toxic or injurious effects on biological systems (Dorland's Medical Dictionary). To determine biocompatibility, the tissue response produced through the close association of the implanted candidate material to its implant site within the host animal may be compared to that tissue response recognized and established as suitable for control materials (e.g., based on standards provided by the American Society for Testing and Materials).

It was determined several years ago, in development of guidewires and cardiovascular stents, that Nitinol is biocompatible despite its 50 atomic percent Ni content. A very thin titanium oxide layer protects the surface.

As described above, Copper is considered to be toxic to tissues and cells. As we have determined and described herein, a single crystal alloy of copper, such as CuAlNi, in which the copper is chemically bound, behaves differently from any one of the individual elemental components.

To determine the extent to which CuAlNi alloy is biocompatible, four series of tests were performed on a single crystal CuAlNi alloy: cytotoxicity, systemic toxicity, hemocompatibility, and implantation with histopathology.

Cytoxicity

Figure 2:
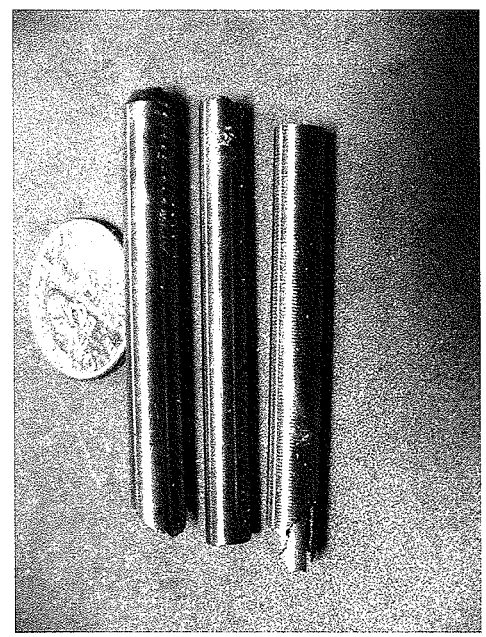
FIG. 2 shows exemplary samples used for the cytotoxicity testing described herein.
Figure 4B:
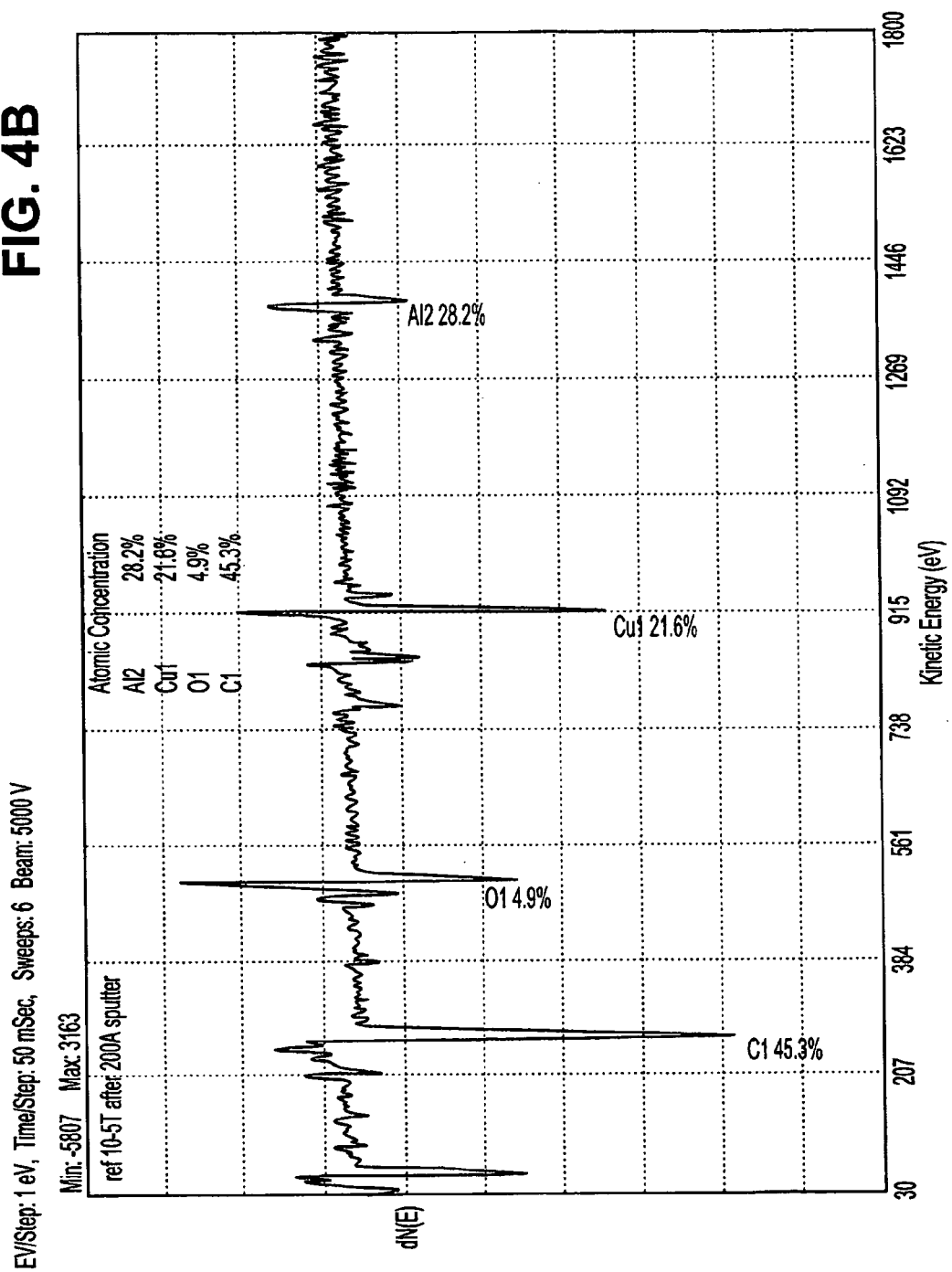
Figure 4F:
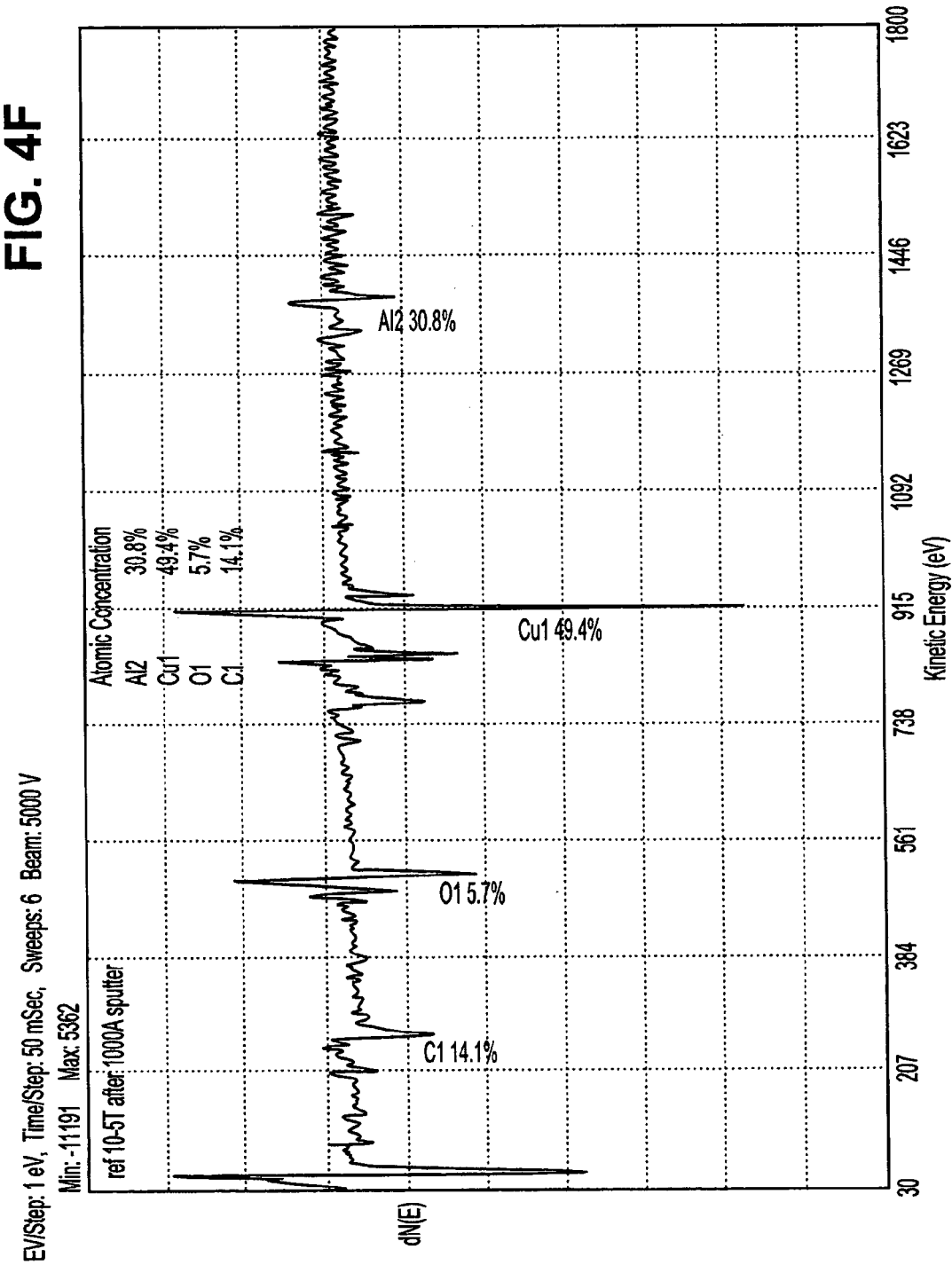
Figure 5A:
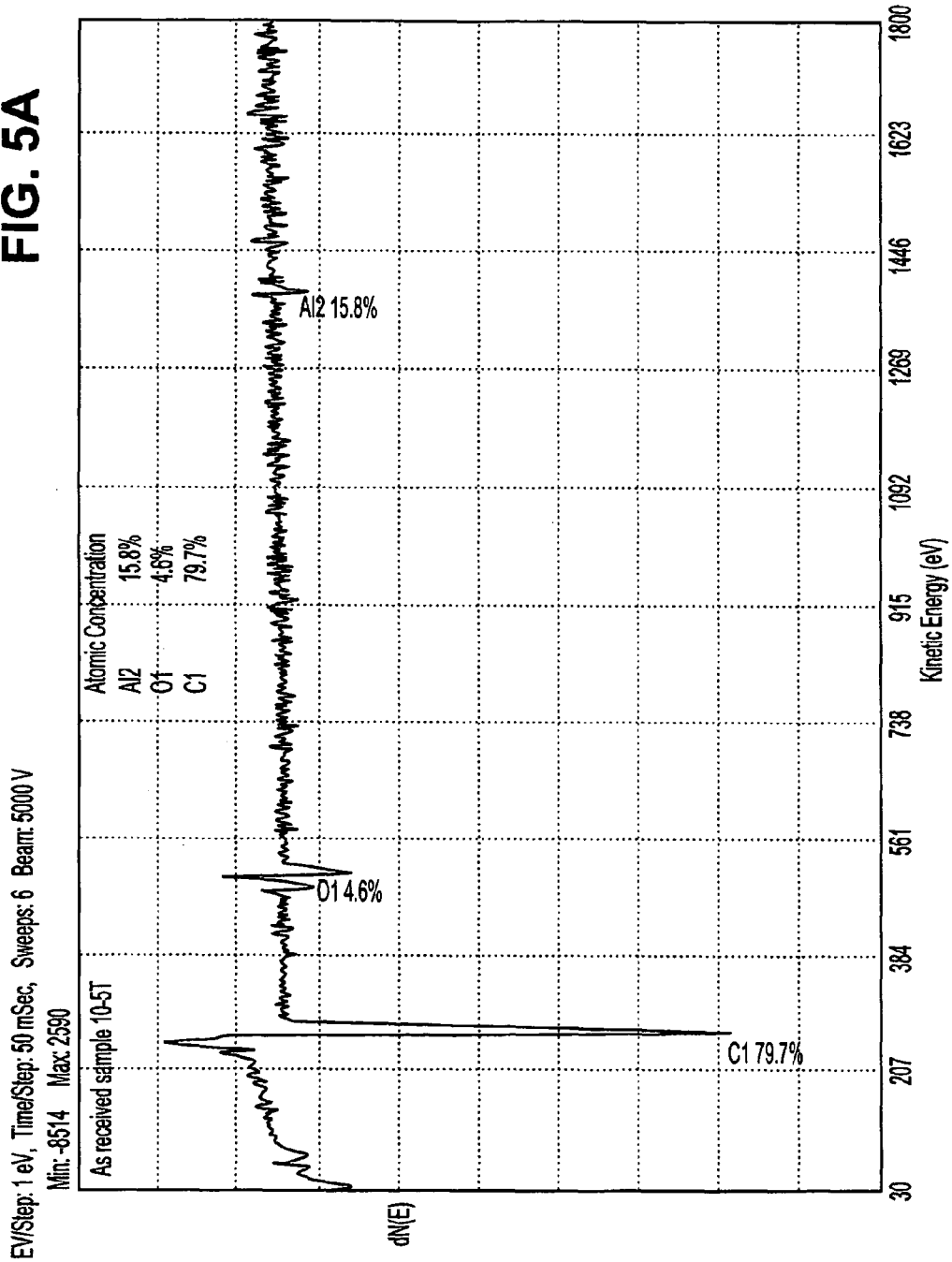
FIGS. 5A-5F show another set of Auger electron spectroscopy (AES) at the surface and at progressively deeper plasma-etched levels (in increments of 200Å, respectively) for a copper-based SMA.
Figure 5B:
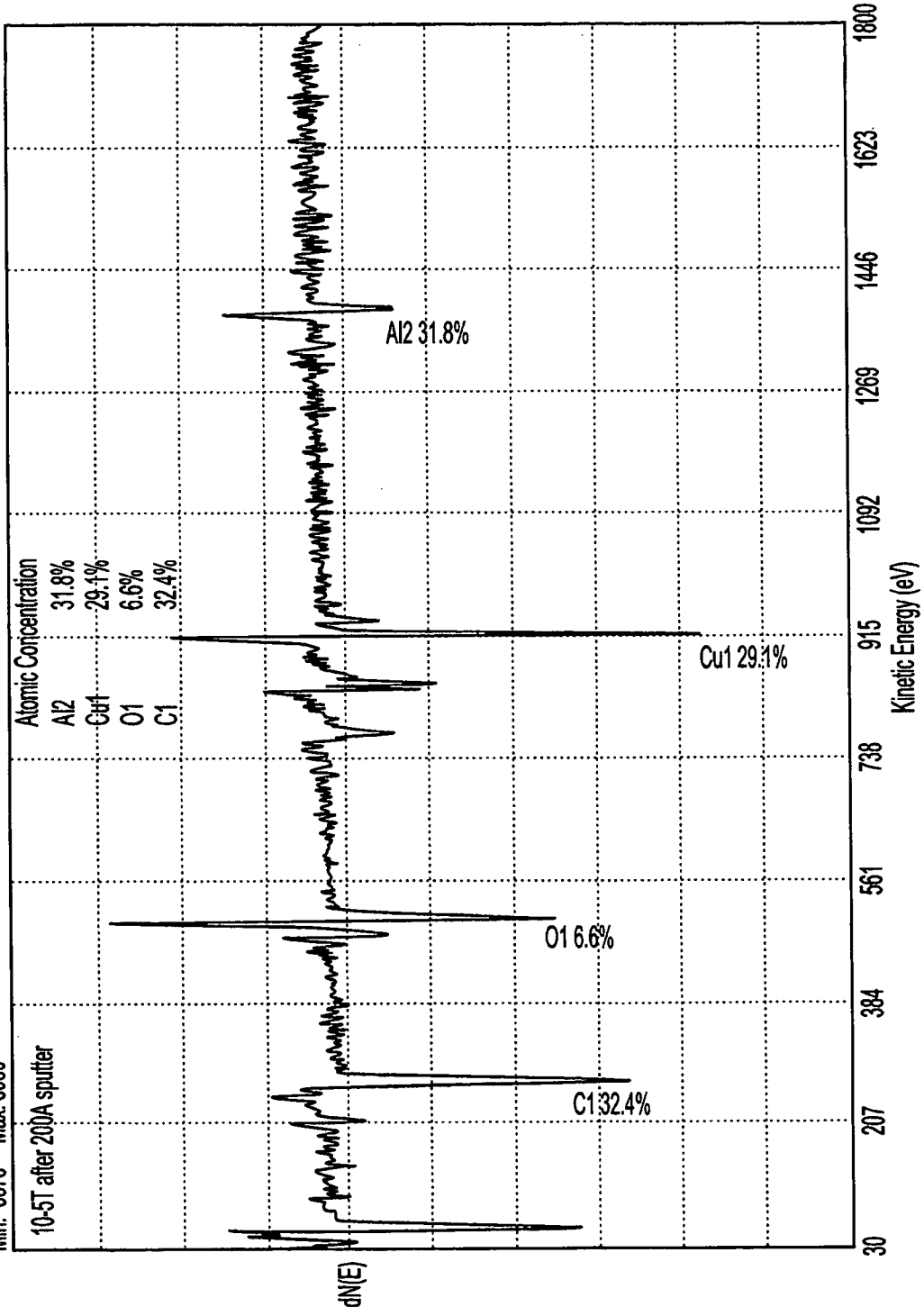
Figure 5C:
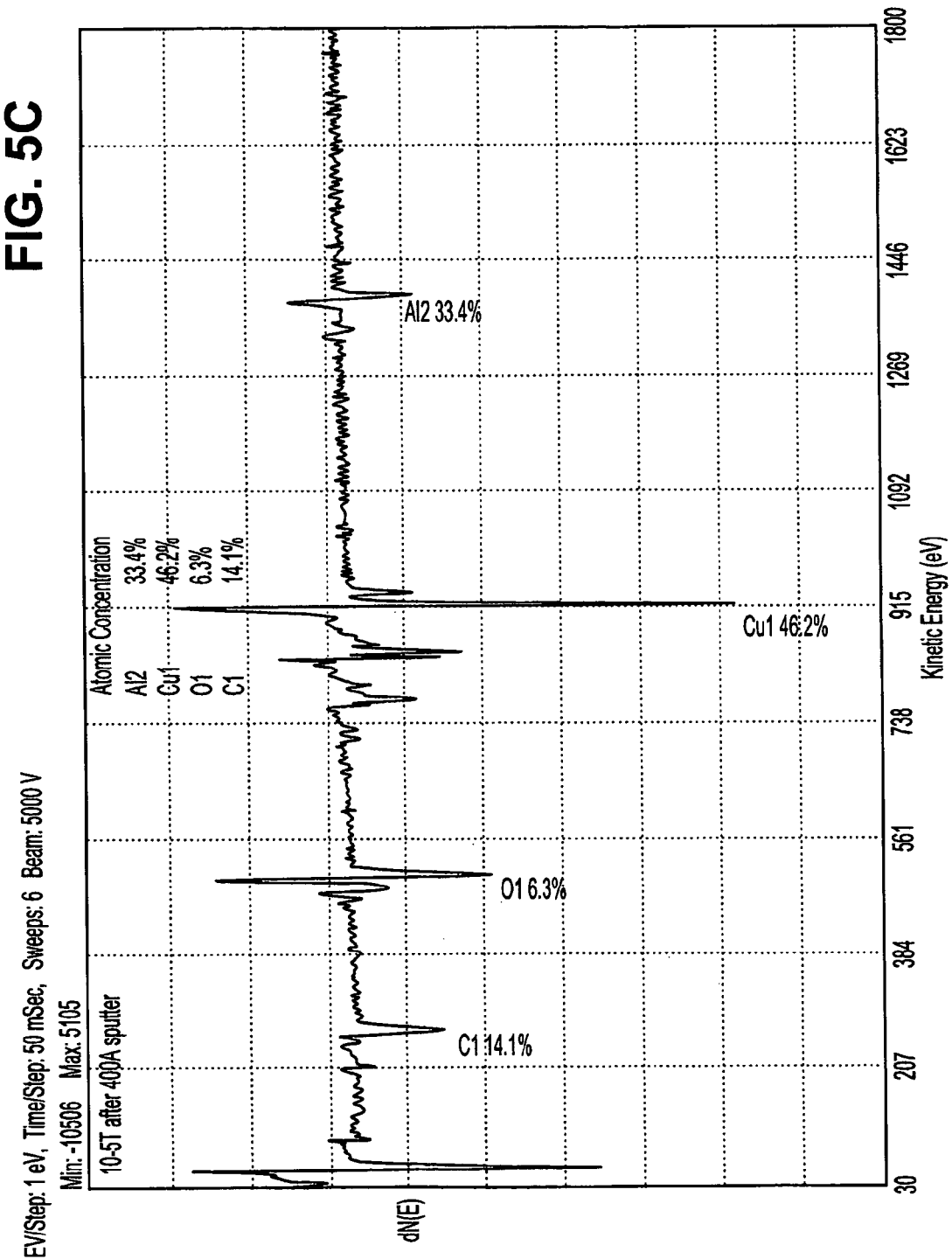
Figure 5D:
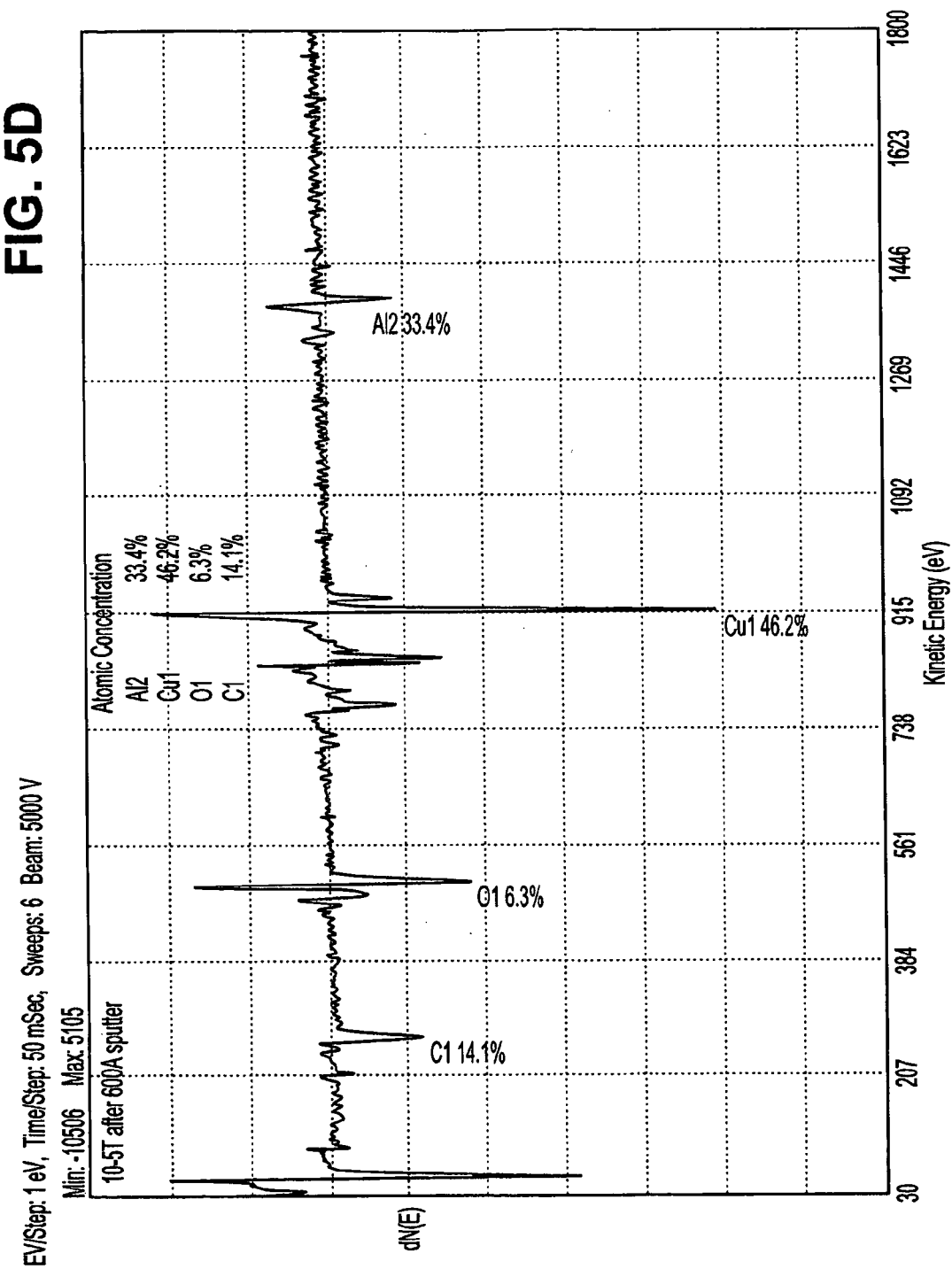
Figure 5E:
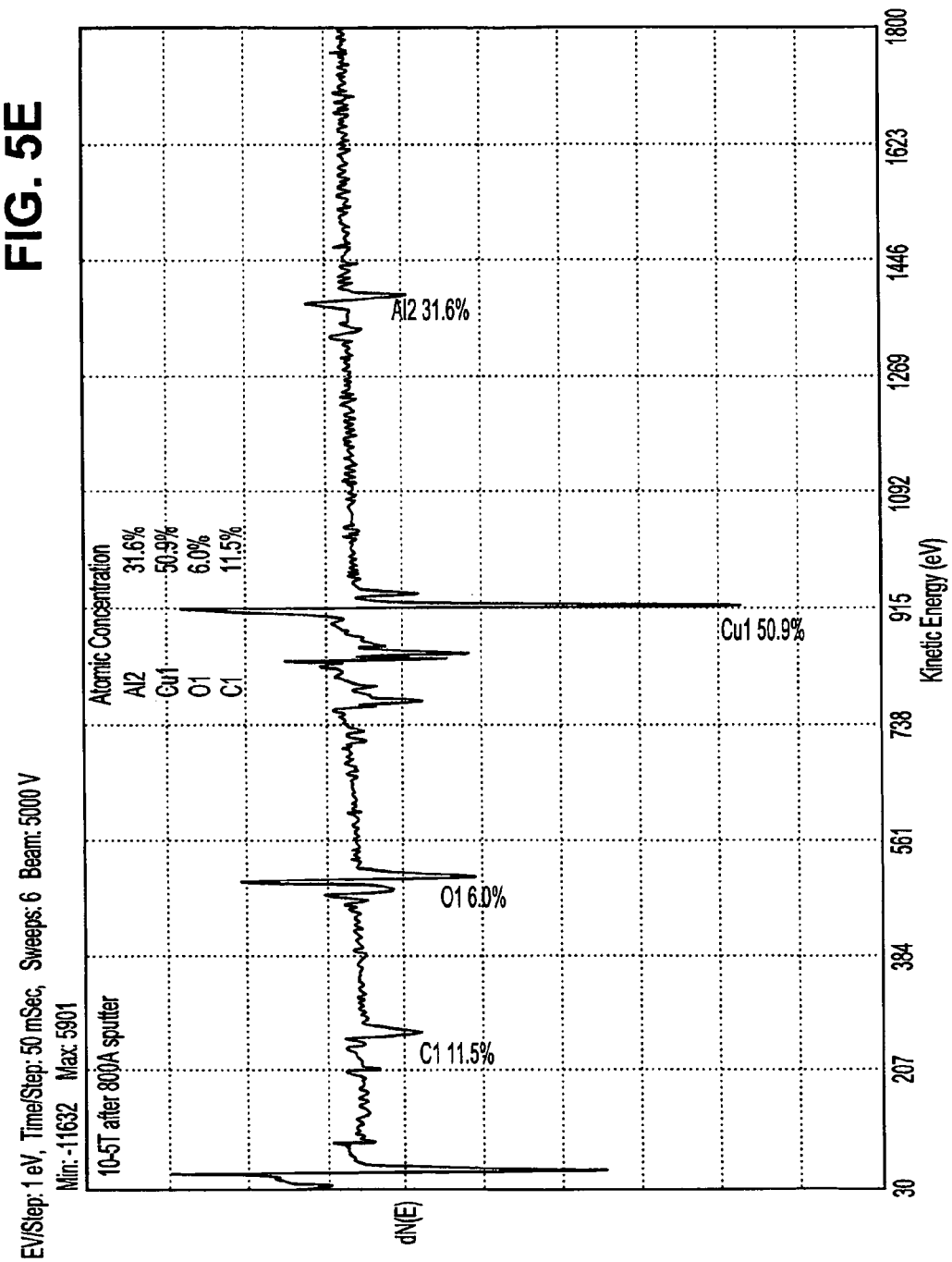
Figure 5F:
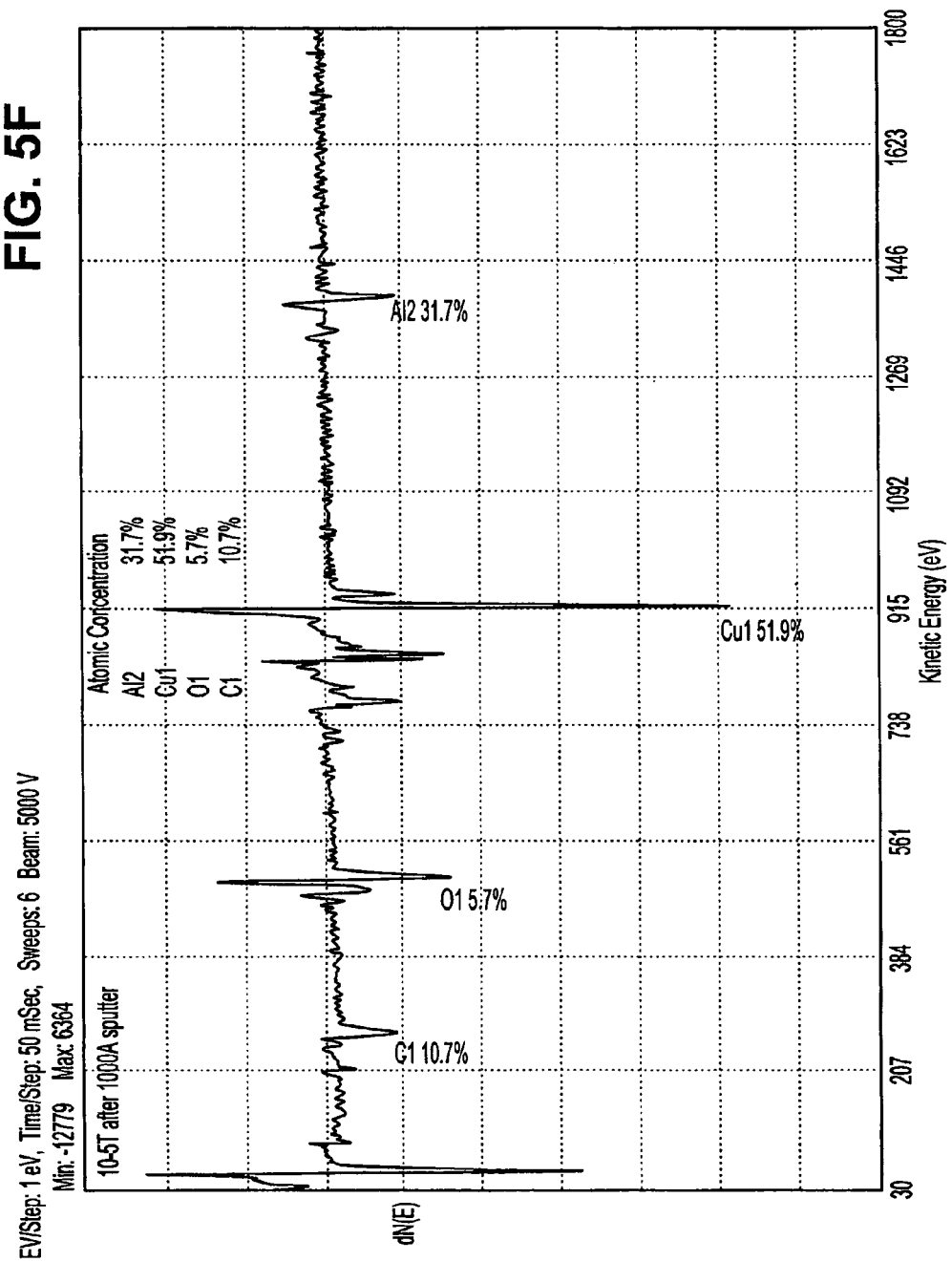
Figure 6B:
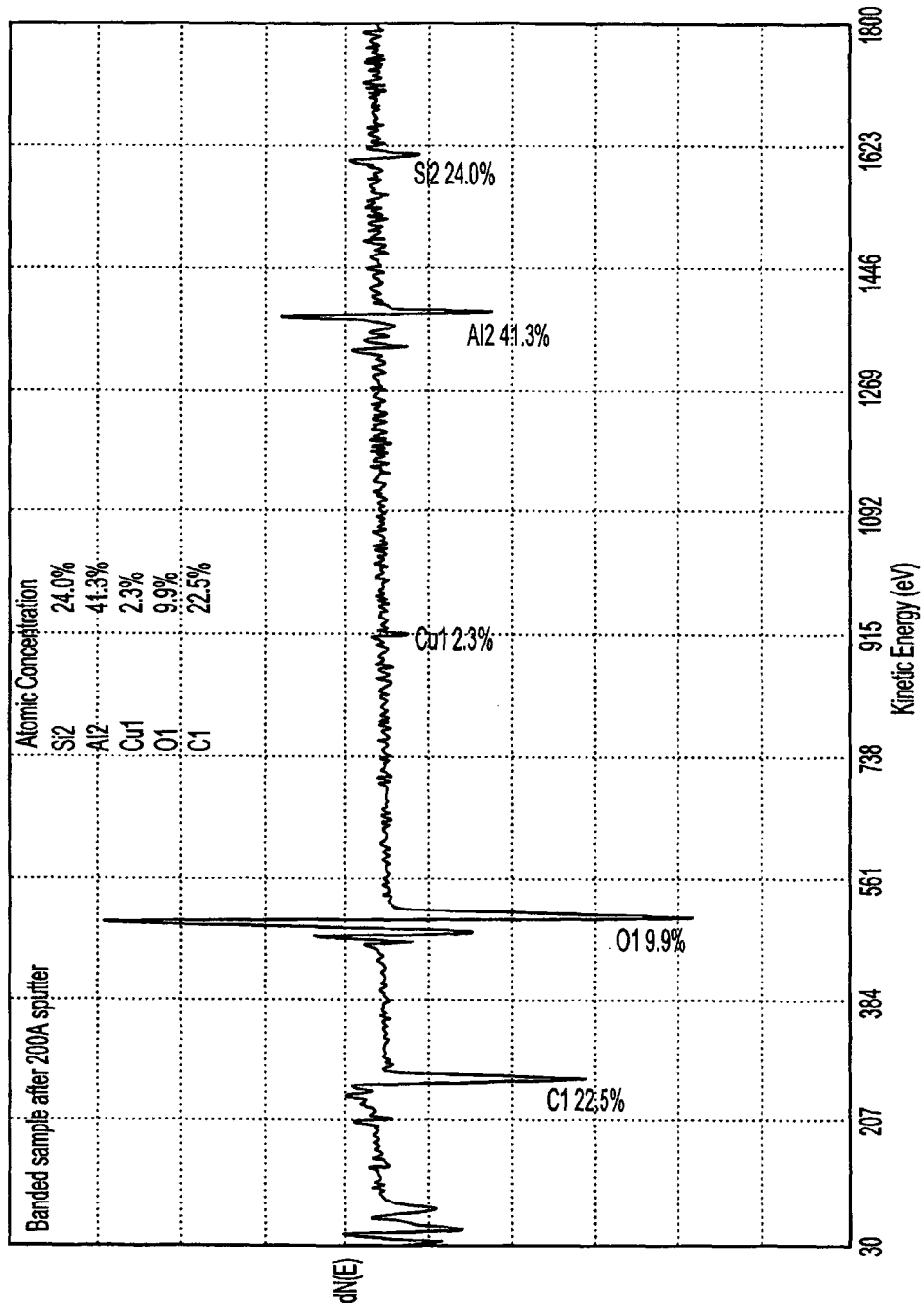
Figure 6C:
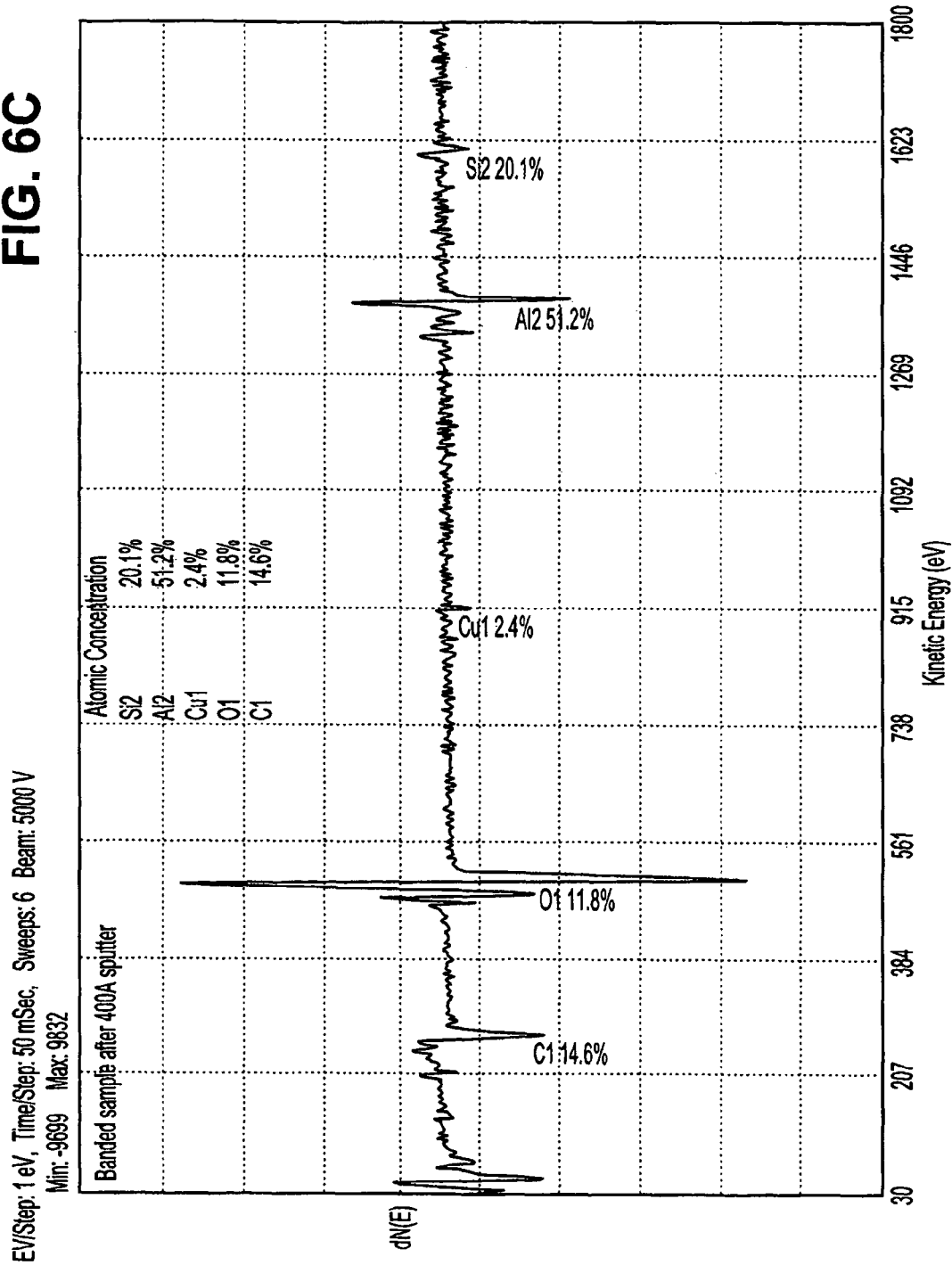
Figure 7A:
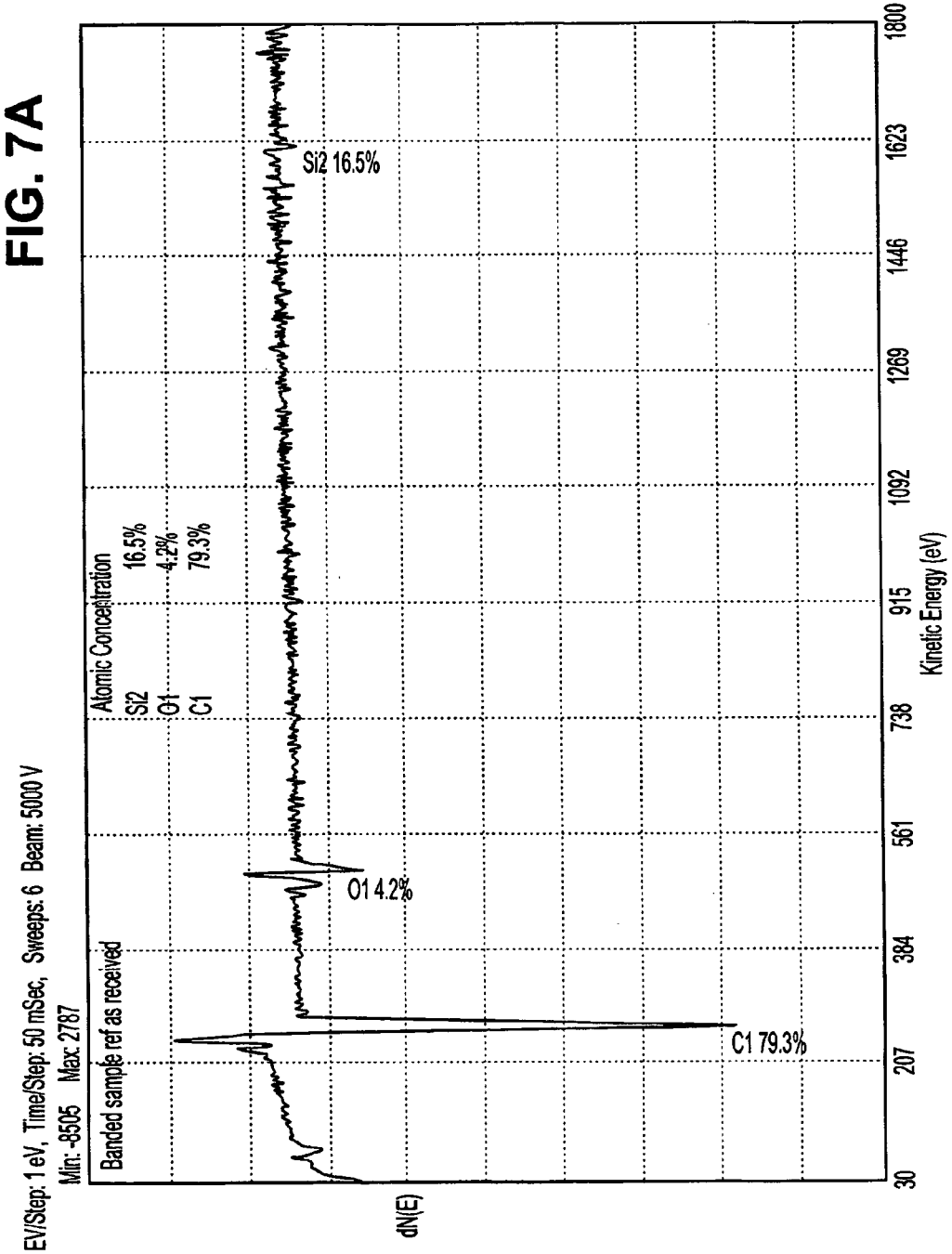
Figure 7D:
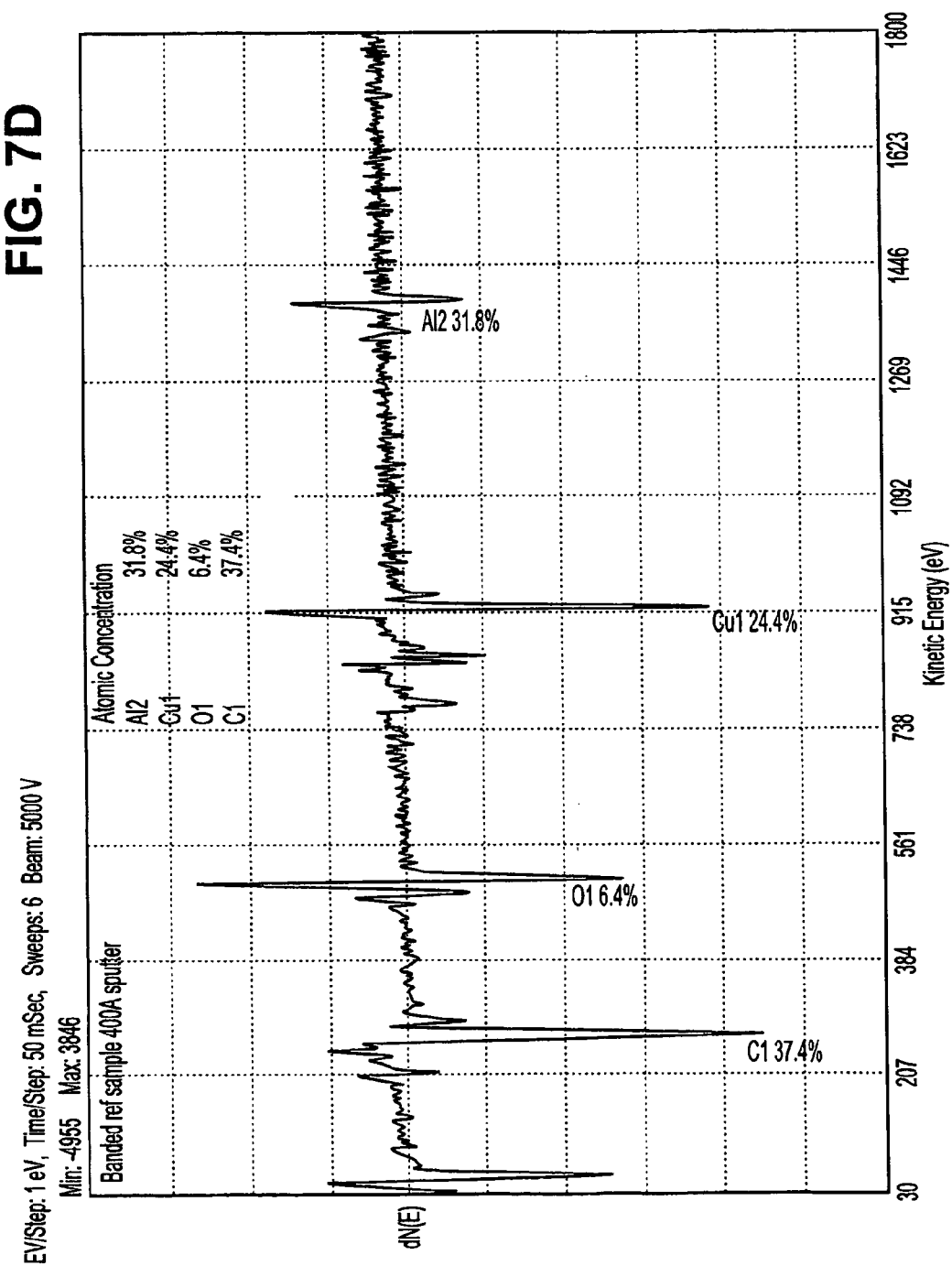
Figure 7E:
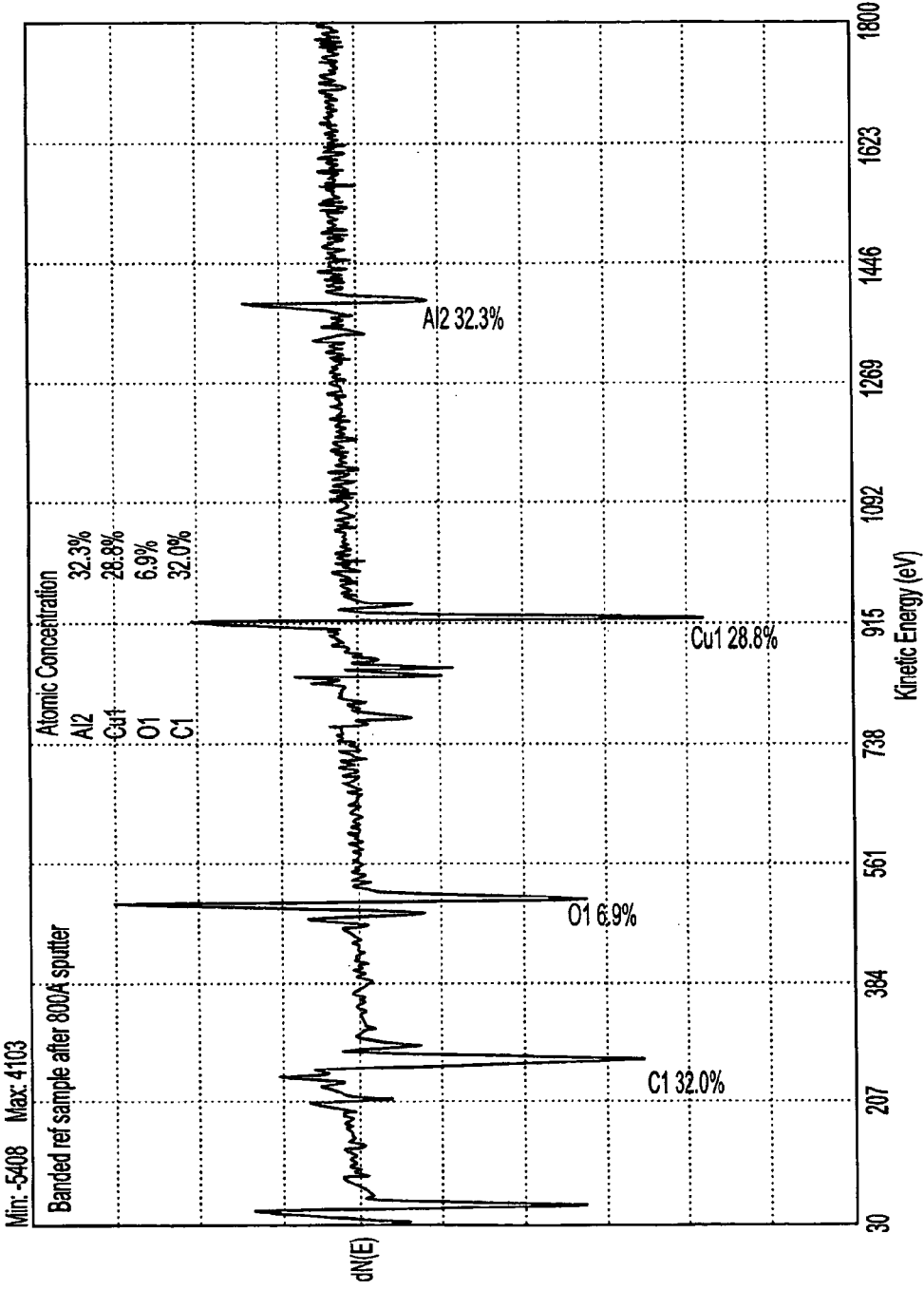
Figure 7F:
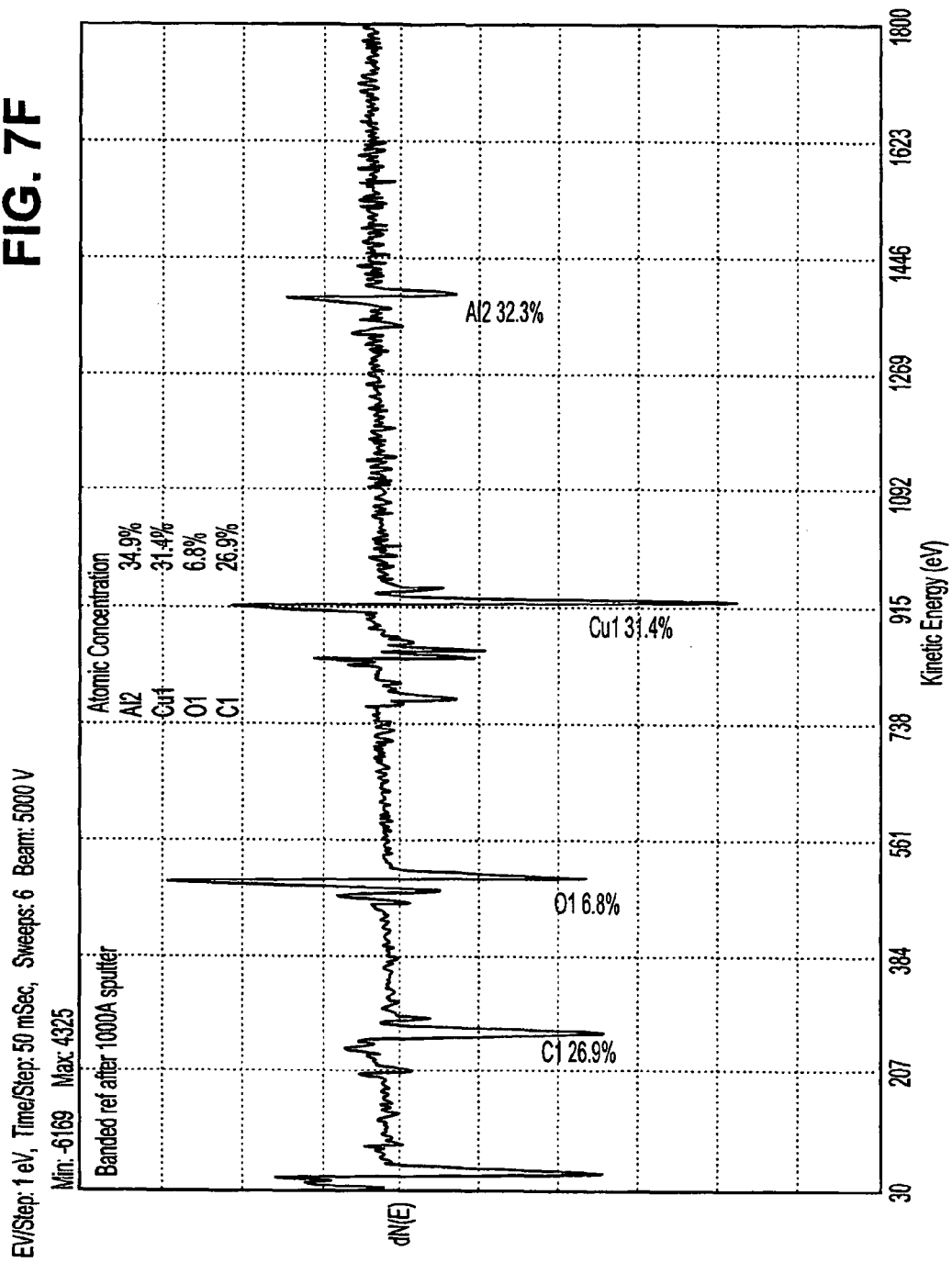

Cytotoxicity testing (ISO 10993-05, USP-87, MEM elution) was performed on CuAlNi rods. The tests were designed to determine the cytotoxicity of extractable substances. An extract of the sample was added to cell monolayers and incubated. The cell monolayers were examined and scored based on the degree of cell destruction. The sample included 9 pieces of 65.2 cm squared (Lab # 267408) CuAlNi rods. Example rods are shown in FIG. 2

The result of these tests was negative for cytotoxicity: cells continued to thrive.

Systemic Toxicity

Systemic toxicity (ISO 10993-11) testing was performed. The purpose of this test was to screen test article extracts for potential toxic effects as a result of a single-dose injection in mice. Groups of five (5) Albino Swiss Mice (*Mus musculus*) were injected systemically with extracts of the test article or control vehicle at a dose rate of 50 mL extract to one kg body weight. The animals were observed for signs of toxicity immediately and at 4, 24, 48 and 72 hours post injection. The test is considered negative if none of the animals injected with the test article extract show a significantly greater biological reaction than the animals treated with the control vehicle extract. A significant biological reaction is interpreted as death in two or more mice or other signs such as convulsions, prostration, or body weight loss greater than 2 grams in three or more mice.

Figure 3:
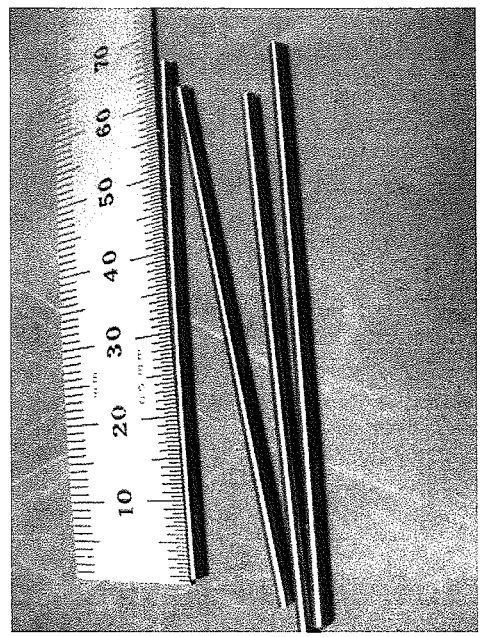
FIG. 3 shows exemplary samples used for the systemic toxicity and hemocompatibility testing.

The samples tested included CuAlNi ("Elastamet™") centerless ground 2 mm diameter 60 mm long (Lab #335379) rods. See FIG. 3.

The result was negative: no harm was done to live animals. The test articles did not produce systemic toxicity under this test.

Hemocompatibility

Hemocompatibility testing (ISO 10993-4; Hcx140) was performed on CuAlNi samples. The procedure uses the general principles outlined in ASTM F 756-00. Extract from sample was incubated with human blood, and a hemolytic index calculated from hemoglobin released.

Samples of CuAlNi were tested using hemolysis Procedure Number STP0093 REV 02 (by Nelson Laboratories, Salt Lake City), which follows general principles of ASTM F 756-00. Human blood was exposed to the alloy and a hemolytic index was calculated. The samples tested (Lab #362047) were similar to those shown in FIG. 3.

The difference between the hemolytic indexes of the test sample and the negative control equals 0.21 percent. This places the test sample in the non-hemolytic range.

Implantation with Histopathology

Implantation with histopathology testing (ISO 10993-6. SCX610) was performed. The purpose of this study was to evaluate the potential toxic effects of a biomaterial in direct contact with living muscle tissue of the rabbit using the standard USP Implantation Test.

AppTec Histology Laboratory performed an ISO 07 day observation with histopathology study to evaluate the local effects of a test article in direct contact with living skeletal muscle tissue. Sections of the test article (CuAlNi rods, Elastamet wire, five pieces, lot #NDM-11, Lab #362046) and control were implanted surgically in the paravertebral muscles of three rabbits. After the exposure period the animals were sacrificed, the paravertebral muscles explanted, the implantation sites were examined grossly for sign of infection, necrosis, discoloration, hemorrhage and also scored for encapsulation. The final analysis of the local effect was based on the histopathology evaluation.

Based on the observations of the histopathologist, the test article was considered a non-irritant.

The negative results of all of these tests implied that the prepared Cu-based SMAs tested are biocompatible, and may be used anywhere that it is deemed useful as it will not harm body tissues by chemical attack in body contact, despite the high copper content.

Preparation of the CU-Based SMA Surface

Biocompatibility and corrosion resistance may be ensured and enhanced by formation of an angstroms-thick layer of aluminum oxide. For example, the samples examined above included a protective outer layer of aluminum oxide. Samples similar to those tested for biocompatibility above were examined by Auger spectroscopy, as illustrated in FIGS. 4A-7F, and show that the surface is enriched in oxygen and aluminum. This layer of aluminum oxide may protect the crystal, and may prevent any adverse affects.

FIGS. 4A-7F show the results of Auger electron spectroscopy (AES) identifying the thin surface layer of aluminum oxide on the outside of the biocompatible copper-based SMAs tested above. The figures show that the surface layer is enriched in Al relative to Cu at least to a depth of 200 Angstroms, (and probably deeper). For example, FIGS. 4A-4F show AES starting at the surface of the sample (as received), in FIG. 4A, and following progressive 200Å sputtering. For example, FIG. 4B is AES after 200Å sputtering, FIG. 4C is AES after 400Å sputtering, FIG. 4D is AES after 600Å sputtering, FIG. 4E is AES after 800Å sputtering and FIG. 4F is AES after 1000Å sputtering. FIGS. 5A-5F show another series of AES following progressive sputtering from the sample shown in FIGS. 4A-4F. Surfaces having a visible dark layer ('banded'), the relative enrichment extends as far as 1000 Angstroms, as shown in FIGS. 6A-6F and again in FIGS. 7A-7F (showing AES at progressive sputtering depths, as indicated). Thus, aluminum in a copper-based SMA may diffuse to the surface and be oxidized, so that it is trapped in the surface in the form of aluminum oxide. Aluminum oxide is typically stable at very high temperatures.

A protective aluminum oxide layer may be formed on the surface of the copper-based SMA when the material is formed (for example, as the crystal is grown and/or when it is quenched). The formation, composition and thickness of this protective surface layer may be controlled to ensure biocompatibility. In particular, surface treatments that are compatible with the formation and maintenance of the protective layer (e.g., of aluminum oxide) that do not damage or interfere with the single crystal copper-based SMA are preferred.

A single-crystal of CuAlNi material, for example, may be prepared by a modified Stepanov method, as described in U.S. patent application Ser. No. 10/588,413 (titled "SINGLE CRYSTAL SHAPE MEMORY ALLOY DEVICES AND METHODS"), herein incorporated in its entirety. In this procedure, a seed of single-crystal SMA alloy (e.g., CuAl-based alloy) is used to pull a length of anisotropic, single crystal shape memory alloy having hyperelastic properties. The ability of a single-crystal to successfully seed a single-crystal pull has been found to be highly dependent on the quality of the seed crystal. In practice it is highly difficult to determine if a particular seed crystal will successfully work; visual inspection does not provide sufficient indication, as even crystals that appear to be good visually may fail to produce a successful pull. Methods of forming single-crystal copper-aluminum alloys that overcome this non-trivial difficulty are described in U.S. patent application Ser. No. 11/243,519 ("METHODS OF ALLOYING REACTIVE COMPONENTS"), herein incorporated by reference in its entirety. These methods may include forming the seed from controlled layers that are reacted together.

The anisotropic single crystal shape memory alloy material formed is deformable at a constant force at recoverable strain of at least 9% with a very narrow loading-unloading hysteresis, a recovery which is completely repeatable and complete and a very low yield strength when martensitic. The seed of copper aluminum based alloy is dipped into a molten melt of a copper aluminum based alloy, wherein the seed is aligned on the <100>crystallographic direction that is the same as the direction of pulling. A column of material is then pulled (to any desired length of the alloy) from the melt by pulling at a predetermined pulling rate so that the rising column is cooled relative to the melt, to form a crystallization front above the surface of the melt, wherein the melt has a composition so that the pulled single crystal column has a transition temperature from martensite to austenite that is below 37 degrees Celsius. The melt is kept at a constant temperature. A predetermined hydrostatic pressure may be applied on the column and the column may be heated to a predetermined temperature, the predetermined pulling rate, hydrostatic pressure and temperature being sufficient to crystallize the alloy in the column into a single crystal. After pulling, the column of single crystal material may be rapidly quenched.

During this formation process, the material may be treated or coated to form the appropriately controlled layer of aluminum oxide. For example, additional Al may be added to the pulled column after is has been pulled from the melt, to enhance the amount of Al on the outer layers of the material that may be available for the aluminum oxide coating. This may be particularly important for alloys having a relatively small percentage of Aluminum (e.g., less than 15%, less than 10%, etc.). In some variations, a stream of reactive gas (e.g., oxygen gas) or plasma may be applied, or any other appropriate coating methods, including those described herein. Alternatively, the material may be coated after formation during post-processing.

The chemical resistance of the appropriately coated single crystal CuAlNi alloys examined here is greater than would be expected, which may be in part due to the layer of aluminum oxide. For example, a single crystal copper-based SMA may have a higher resistance to corrosion due to the surface layer of Aluminum oxide. Several very preliminary observations regarding aging and corrosion resistance include:

Corrosion in air. After centerless grinding of the single crystal CuAlNi, the surface is bright. This gradually turns darker over months of exposure to room air. This is most noticeable on samples not carefully cleaned. Electropolished samples may remain bright for many months (the brightness may be copper color).

Salt water. Parts immersed in seawater for 24 months became covered with black, but part appears to be undamaged.

Preliminary experiments looking at corrosion: parts immersed in strong acids and bases for several months are differently affected. Sulphuric acid gradually eroded the surface, leaving it a bright copper color; nitric acid dissolved the sample after several weeks; HCL solution turns blue after several months, and sample shows damage;

KOH has no noticeable effect.

Methods of Treating Copper-Based SMA

Copper-based SMAs may be treated in various ways, including treatments to form and enhance the protective surface layer (e.g., aluminum oxide layer). For example, during the formation of a copper-based SMA alloy, the quenching step may be used to create an appropriate oxide protective layer.

In some variations, the surface of the copper-based SMA may be electropolished to create ultrasmooth surface. Further processing may be used to enhance biocompatibility. In some variations, shape-setting by rapid heating and cooling may be used. In some variations, the material may be electropolished by treatment using a relatively low voltage (e.g., in the order of 10-20 volts), with a concentrated solution of acid (e.g. glacial acetic acid) and an oxidizer (e.g. chromium trioxide).

A protective layer of aluminum oxide may be controllably added by a number of processes, including those described herein, such as increasing the surface concentration of aluminum (e.g., by doping the surface, or enhancing diffusion to the surface, etc.), anodizing, plasma electrolytic oxidation, or the like. Although a layer of aluminum oxide may be formed as a byproduct during the processes for forming the single crystal alloy by the subsequent heating and 'quenching' used in forming the alloy, the layer is typically uneven, and the actual thickness may be insufficient to convey durable biocompatibility and resistance to corrosion. Thus, it is highly advantageous to provide a deliberate process to create a layer of aluminum oxide (e.g., nanometer-thick or greater) for the purpose of enhancing the properties of the copper-based SMA. In some variations, the surface layer of aluminum oxide is greater than 1 nm thick, greater than 10 nm thick, or greater than 100 nm thick.

As mentioned above, the surface of the copper-based SMA may be prepared in order to enhance the aluminum oxide layer. For example, the surface may be polished or ground (e.g., by centerless grinding, electropolishing, etc.). Preparing the surface may also allow further control over the thickness and distribution of the aluminum oxide layer.

In some variations, the thickness of the aluminum oxide layer is non-uniform, but is instead controlled so that it is thicker in regions of the device that may require additional protection or biocompatibility. For example, regions of the device that are configured to displace more than other regions (e.g., regions having a smaller cross-sectional area) may include a thicker protective coating, which may resist wear or disruption during the normal use of the device.

One way to control the thickness and/or distribution of the aluminum oxide layer is to control the concentration and/or distribution of aluminum near the surface of the copper-based SMA. For example, the percentage of Al near all or a portion of the surface of a single crystal device may be enhanced. In one variation, a single crystal copper-based SMA is formed with a controlled (e.g., relatively small) percentage of Al in the alloy, and then the alloy is soaked an Al-rich environment at a high enough temperature for the Al atoms to diffuse to the surface. This surface (or near-surface) Al may then be oxidized. In some variations, a layer of Al may be deposited on the surface of the single crystal SMA, the surface can be heated to cause diffusion of Al atoms into the surface, and an aluminum oxide layer can then be formed using the "doped" Al.

The thickness and properties of the oxide layer may also be enhanced or controlled in a process similar to anodizing, by the application of electrical voltage to the device (e.g., electrolytic passivation).

In one variation, plasma electrolytic oxidation may be used to coat (or enhance the coating of) aluminum oxide on the copper-based SMA. This may be achieved by the application of relatively high voltages.

In general, the crystalline form of the aluminum oxide may be controlled. For example, the surface of the copper-based SMA may be partially or completely coated with an amorphous aluminum oxide layer. In other variations, the aluminum oxide layer on the surface of a single crystal copper-based SMA maybe predominantly (or completely) crystalline aluminum oxide. The crystalline form of aluminum oxide included on the surface of the copper-based SMA may depend on the intended use. For example, crystalline aluminum oxide may enhance the surface strength and corrosion resistance. Amorphous aluminum oxide may be preferred in some variations in which the SMA will undergo substantial recoverable deformation.

In some variations, an additional coating layer (e.g., sealant, etc.) may also be applied. For example, the surface of the SMA may be sealed to further enhance corrosion resistance.

Uses of Biocompatible Copper-Based SMAs

As described above, single crystal copper-based SMAs, particularly those having a protective layer of aluminum oxide (and any additional coating) may be used as part of any appropriate biomedical device, particularly implants. In general, hyperelastic shape memory alloys such as single crystal copper-based SMAs are superior for use in medical applications because of their large recoverable strain at constant stress. One can take advantage of this feature to protect body tissues from damage.

In normal use, metal acts as an elastic material, with minimal displacement. In unusual condition, if stress rises above a critical level, the metal displaces without exerting additional force, and the displacement can be as much as 9 percent strain. This has two advantages: the device is not so likely to fracture, and it protects the bone or other body tissue to which the implanted device is attached from stresses that are beyond its fracture limit.

Thus, devices for use within the human (or other mammalian) body, and particularly those chronically exposed to bodily fluids, may be formed from single crystal copper-based SMAs that are protected by a (controlled) coating of aluminum oxide. Various copper-based SMAs, including Cu+Al+ (Ni or Mn or Be) may be used. These biocompatible alloys may be used to take advantage of their hyperelastic properties (having recoverable strains greater than 8% with a relatively flat stress plateau, as shown in FIG. 1). In particular, devices having a martensitic transformation with $A_f$ between 10 and 40 degrees C. may be useful. Such devices may be useful for intravascular use, for intramuscular use, for intraocular use, etc.

For example, a hip bone replacement may be at least partially formed of a single crystal shape memory device including a protective coating of aluminum oxide, as described herein. Other examples of implants made from such single crystal copper-based devices include joint implants, devices including a guidewire, clot retrievers, blood filters (e.g., embolism filters), stents, dental arches, etc.

The chemical resistance (e.g., to corrosion, etc.) of a single crystal copper-based SMA (e.g., CuAlNi) is greater than would be expected from the chemical contents of the alloy when protected by the aluminum oxide layer. Further the copper-based SMA including the aluminum oxide layer is substantially biocompatible, as suggested by the tests described above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A biocompatible device for use within a body comprising a single crystal copper-based shape memory alloy having an exposed outer surface at and below which resides a surface region of depth greater than 1 nm below the exposed outer surface that is enriched in aluminum relative to copper, wherein the aluminum enriched in the surface region of the single crystal copper-based shape memory alloy is in the form of aluminum oxide thereby forming a protective outer layer comprising aluminum oxide greater than 1 nm thick that is formed at least in part by oxidizing the aluminum enriched in the surface region of the single crystal.

2. The device of claim 1, wherein the single-crystal copper-based shape memory material comprises CuAlNi.

3. The device of claim 1, wherein the protective outer layer comprising aluminum oxide is an amorphous layer of aluminum oxide.

4. The device of claim 1, wherein the protective outer layer comprising aluminum oxide is substantially crystalline aluminum oxide.

5. The device of claim 1, wherein the protective outer layer comprising aluminum oxide is greater than 100 nm thick.

6. The device of claim 1, wherein the single crystal copper-based shape memory alloy is configured as at least one of: a joint replacement, a hip bone replacement, a guidewire, a clot retriever, a blood filter, a stent, and a dental arch.

7. The device of claim 1, wherein the depth of the surface region is greater than 10 nm below the exposed outer surface.

8. A method of forming the biocompatible device of claim 1, the method comprising the steps of:

forming the single crystal copper-based shape memory alloy from a seed of copper aluminum based alloy aligned on the <100>crystallographic direction; and forming the protective outer layer comprising aluminum oxide in the surface region of the single crystal copper-based shape memory alloy by a controlled process of doping the surface region with Al after forming the single crystal copper-based shape memory alloy, anodizing the surface region of the single crystal copper-based shape memory alloy, and/or applying a high voltage to the single crystal copper-based shape memory alloy.

9. A biocompatible dental arch comprising a copper-aluminum single crystal shape memory alloy having an exposed outer surface from which extends a surface region of depth greater than 1 nm below the outer surface of the single crystal shape memory alloy that is enriched in aluminum relative to copper, wherein the surface region provides a protective outer layer comprising aluminum oxide formed at least in part by oxidizing the aluminum enriched in the surface region of the single crystal.

10. The device of claim 9, wherein the protective outer layer comprising aluminum oxide is greater than 10 nm thick.

11. The device of claim 9, wherein the single-crystal copper-based shape memory material comprises CuAlNi, and the protective outer layer comprising aluminum oxide is an amorphous layer of aluminum oxide of thickness greater than 100 nm.

12. The device of claim 9, wherein the single-crystal copper-based shape memory material comprises CuAlNi, and the protective outer layer comprising aluminum oxide is substantially crystalline aluminum oxide of thickness greater than 100 nm.

* * * * *

UNITED STATES PATENT AND TRADEMARK OFFICE
CERTIFICATE OF CORRECTION

| | |
|---|---|
| PATENT NO. | : 8,556,969 B2 |
| APPLICATION NO. | : 12/325722 |
| DATED | : October 15, 2013 |
| INVENTOR(S) | : Alfred David Johnson |

It is certified that error appears in the above-identified patent and that said Letters Patent is hereby corrected as shown below:

In the Specification

Col. 2, lines 23-24, "hemo-compatibility tests were performed to show" should read --hemo-compatibility tests performed show--.

Col. 3, line 31, the following paragraph was omitted and should be added --The step of forming the single crystal copper-based shape memory alloy may include forming a single crystal CuAlNi alloy.--.

Col. 4, line 51, "medical practice that will" should read --medical practice will--.

Col. 5, line 30, "are shown in FIG. 2" should read --are shown in FIG. 2.--.

Col. 6, line 39, "any adverse affects." should read --any adverse effects.--.

Col. 7, line 49, "column after is has been" should read --column after it has been--.

Col. 9, line 2, "soaked an Al-rich environment" should read --soaked in an Al-rich environment--.

In Col. 9, line 23, "SMA maybe predominantly" should read --SMA may be predominantly--.

Signed and Sealed this
First Day of July, 2014

Michelle K. Lee
*Deputy Director of the United States Patent and Trademark Office*